(12) United States Patent
Chen et al.

(10) Patent No.: US 12,297,425 B2
(45) Date of Patent: May 13, 2025

(54) NUCLEIC ACID EXTRACTION COMPOSITION, REAGENT AND KIT CONTAINING THE SAME AND USE THEREOF

(71) Applicants: Capitalbio Corporation, Beijing (CN); West China Hospital of Sichuan University, Sichuan (CN)

(72) Inventors: Xiang Chen, Beijing (CN); Lei Wang, Beijing (CN); Su Li, Beijing (CN); Longtang Zheng, Beijing (CN); Yanan Wang, Beijing (CN); Fei Wen, Beijing (CN); Juan Xin, Beijing (CN); Wentian Zhang, Beijing (CN); Jing Cheng, Beijing (CN)

(73) Assignees: CAPITALBIO CORPORATION, Beijing (CN); WEST CHINA HOSPITAL OF SICHUAN UNIVERSITY, Sichuan (CN)

( * ) Notice: Subject to any disclaimer, the term of this patent is extended or adjusted under 35 U.S.C. 154(b) by 1057 days.

(21) Appl. No.: 17/237,495

(22) Filed: Apr. 22, 2021

(65) Prior Publication Data
US 2021/0332348 A1   Oct. 28, 2021

(30) Foreign Application Priority Data
Apr. 28, 2020  (CN) .......................... 202010347016.5

(51) Int. Cl.
*C12N 15/10* (2006.01)
*C12Q 1/6806* (2018.01)

(52) U.S. Cl.
CPC ....... *C12N 15/1006* (2013.01); *C12Q 1/6806* (2013.01)

(58) Field of Classification Search
CPC ................................................ C12N 15/1006
See application file for complete search history.

(56) References Cited

U.S. PATENT DOCUMENTS

| | | |
|---|---|---|
| 7,888,006 B2 | 2/2011 | Lenz |
| 2019/0062802 A1 | 2/2019 | Boone et al. |

FOREIGN PATENT DOCUMENTS

| | | |
|---|---|---|
| CN | 101285062 A | 10/2008 |
| CN | 106085973 A | 11/2016 |
| CN | 106701741 A | 5/2017 |
| CN | 108774619 A | 11/2018 |
| CN | 109182332 A | 1/2019 |
| CN | 109207476 A | 1/2019 |
| CN | 109439656 A | 3/2019 |
| CN | 109722431 A | 5/2019 |
| CN | 110343601 A | 10/2019 |
| CN | 110452902 A | 11/2019 |
| CN | 110684764 A | 1/2020 |
| EP | 1 529 841 A1 | 5/2005 |
| EP | 1529840 A1 | 5/2005 |
| TW | 201213805 A | 4/2012 |
| WO | WO 2004/108741 A1 | 12/2004 |
| WO | WO 2005/012523 A1 | 2/2005 |
| WO | WO 2013/148346 A1 | 10/2013 |

OTHER PUBLICATIONS

Extended European Search Report in European Patent Application No. 21168496.4 issued Sep. 10, 2021.

*Primary Examiner* — Suzanne M Noakes
(74) *Attorney, Agent, or Firm* — Knobbe, Martens, Olson & Bear, LLP

(57) ABSTRACT

A nucleic acid extraction composition, reagents and kits containing the same and uses thereof. Provided is a nucleic acid extraction and purification reagent free of volatile organic solvents, which prevents the damage of volatile organic solvents to people and greatly improves the timeliness of nucleic acid extraction and purification, making the operation extremely simple, and the nucleic acid can be obtained within 10 minutes. The obtained nucleic acid may be used for biological reactions such as PCR, NASBA, LAMP and RPA. Moreover, the reagents of the present disclosure may be used to extract nucleic acids of cells, bacteria, fungi, DNA viruses and RNA viruses from various samples such as blood, throat swab preserving fluid, saliva, urine, sputum, excrement and the like, and very suitable for clinical and scientific research uses.

4 Claims, 22 Drawing Sheets

Specification includes a Sequence Listing.

A

B

C

D

A

B

A

B

C

A

B

C

D

A

B

C

D

A

B

C

D

C

D

C

A

B

C

D

E

F

A

B

C

SEQUENCE LISTING

<160> NUMBER OF SEQ ID NOS: 56

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
tgcgagtgct tatcaatggt                                              20

<210> SEQ ID NO 2
<211> LENGTH: 19
<212> TYPE: DNA
<213> ORGANISM: Artificial
<220> FEATURE:
<223> OTHER INFORMATION: Primer

<400> SEQUENCE: 2
agttctggtt acgcatcgg                                               19

<210> SEQ ID NO 3
<211> LENGTH: 42
<212> TYPE: DNA
<213> ORGANISM: Artificial
<220> FEATURE:
<223> OTHER INFORMATION: Primer

```
<400> SEQUENCE: 3
actgagaacg tgcccatcat gtatcccaca ttcggagaac ac                42

<210> SEQ ID NO 4
<211> LENGTH: 39
<212> TYPE: DNA
<213> ORGANISM: Artificial
<220> FEATURE:
<223> OTHER INFORMATION: Primer

<400> SEQUENCE: 4
ctgtggggac ctccaagtcc aaggtatcca cgccctgac                   39

<210> SEQ ID NO 5
<211> LENGTH: 25
<212> TYPE: DNA
<213> ORGANISM: Artificial
<220> FEATURE:
<223> OTHER INFORMATION: Primer

<400> SEQUENCE: 5
cgtattcaag atctttctcc tgttt                                  25

<210> SEQ ID NO 6
<211> LENGTH: 23
<212> TYPE: DNA
<213> ORGANISM: Artificial
<220> FEATURE:
<223> OTHER INFORMATION: Primer

<400> SEQUENCE: 6
agtacccttt agtggttagg att                                    23

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
tgcgagtgct tatcaatggt                                        20

<210> SEQ ID NO 8
<211> LENGTH: 19
<212> TYPE: DNA
<213> ORGANISM: Artificial
<220> FEATURE:
<223> OTHER INFORMATION: Primer

<400> SEQUENCE: 8
agttctggtt acgcatcgg                                         19

<210> SEQ ID NO 9
<211> LENGTH: 42
<212> TYPE: DNA
<213> ORGANISM: Artificial
<220> FEATURE:
<223> OTHER INFORMATION: Primer

<400> SEQUENCE: 9
actgagaacg tgcccatcat gtatcccaca ttcggagaac ac                42

<210> SEQ ID NO 10
<211> LENGTH: 39
```

```
<212> TYPE: DNA
<213> ORGANISM: Artificial
<220> FEATURE:
<223> OTHER INFORMATION: Primer

<400> SEQUENCE: 10
ctgtggggac ctccaagtcc aaggtatcca cgccctgac                              39

<210> SEQ ID NO 11
<211> LENGTH: 25
<212> TYPE: DNA
<213> ORGANISM: Artificial
<220> FEATURE:
<223> OTHER INFORMATION: Primer

<400> SEQUENCE: 11
cgtattcaag atctttctcc tgttt                                             25

<210> SEQ ID NO 12
<211> LENGTH: 23
<212> TYPE: DNA
<213> ORGANISM: Artificial
<220> FEATURE:
<223> OTHER INFORMATION: Primer

<400> SEQUENCE: 12
agtacccttt agtggttagg att                                               23

<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13
tgcgagtgct tatcaatggt                                                   20

<210> SEQ ID NO 14
<211> LENGTH: 19
<212> TYPE: DNA
<213> ORGANISM: Artificial
<220> FEATURE:
<223> OTHER INFORMATION: Primer

<400> SEQUENCE: 14
agttctggtt acgcatcgg                                                    19

<210> SEQ ID NO 15
<211> LENGTH: 42
<212> TYPE: DNA
<213> ORGANISM: Artificial
<220> FEATURE:
<223> OTHER INFORMATION: Primer

<400> SEQUENCE: 15
actgagaacg tgcccatcat gtatcccaca ttcggagaac ac                          42

<210> SEQ ID NO 16
<211> LENGTH: 39
<212> TYPE: DNA
<213> ORGANISM: Artificial
<220> FEATURE:
<223> OTHER INFORMATION: Primer

<400> SEQUENCE: 16
```

```
ctgtggggac ctccaagtcc aaggtatcca cgccctgac                                 39
```

<210> SEQ ID NO 17
<211> LENGTH: 25
<212> TYPE: DNA
<213> ORGANISM: Artificial
<220> FEATURE:
<223> OTHER INFORMATION: Primer

<400> SEQUENCE: 17

```
cgtattcaag atctttctcc tgttt                                                25
```

<210> SEQ ID NO 18
<211> LENGTH: 23
<212> TYPE: DNA
<213> ORGANISM: Artificial
<220> FEATURE:
<223> OTHER INFORMATION: Primer

<400> SEQUENCE: 18

```
agtacccttt agtggttagg att                                                  23
```

<210> SEQ ID NO 19
<211> LENGTH: 22
<212> TYPE: DNA
<213> ORGANISM: Artificial
<220> FEATURE:
<223> OTHER INFORMATION: Primer

<400> SEQUENCE: 19

```
acataccaag ttatgcagat ga                                                   22
```

<210> SEQ ID NO 20
<211> LENGTH: 19
<212> TYPE: DNA
<213> ORGANISM: Artificial
<220> FEATURE:
<223> OTHER INFORMATION: Primer

<400> SEQUENCE: 20

```
cctccgaacg atatgcttc                                                       19
```

<210> SEQ ID NO 21
<211> LENGTH: 55
<212> TYPE: DNA
<213> ORGANISM: Artificial
<220> FEATURE:
<223> OTHER INFORMATION: Primer

<400> SEQUENCE: 21

```
ctacctcttg accctgatta tttgtaagct tagattatct agtttgtggg aacag               55
```

<210> SEQ ID NO 22
<211> LENGTH: 49
<212> TYPE: DNA
<213> ORGANISM: Artificial
<220> FEATURE:
<223> OTHER INFORMATION: Primer

<400> SEQUENCE: 22

```
actctaatag cgcaataact ctcctgaatt cttaccacaa accccaagc                      49
```

<210> SEQ ID NO 23
<211> LENGTH: 24
<212> TYPE: DNA
<213> ORGANISM: Artificial

<220> FEATURE:
<223> OTHER INFORMATION: Primer

<400> SEQUENCE: 23
catcttgaaa caacgcacta gttc                                    24

<210> SEQ ID NO 24
<211> LENGTH: 25
<212> TYPE: DNA
<213> ORGANISM: Artificial
<220> FEATURE:
<223> OTHER INFORMATION: Primer

<400> SEQUENCE: 24 tttttctct gtattgcgtg tacgg                                    25

<210> SEQ ID NO 25
<211> LENGTH: 18
<212> TYPE: DNA
<213> ORGANISM: Artificial
<220> FEATURE:
<223> OTHER INFORMATION: Primer

<400> SEQUENCE: 25
tatatacagt aaagacaa                                           18

<210> SEQ ID NO 26
<211> LENGTH: 19
<212> TYPE: DNA
<213> ORGANISM: Artificial
<220> FEATURE:
<223> OTHER INFORMATION: Primer

<400> SEQUENCE: 26
agagggaact tcaccaata                                          19

<210> SEQ ID NO 27
<211> LENGTH: 44
<212> TYPE: DNA
<213> ORGANISM: Artificial
<220> FEATURE:
<223> OTHER INFORMATION: Primer

<400> SEQUENCE: 27
attccaaggg ggagcatgat atcagtgtaa gaatcggttc caag              44

<210> SEQ ID NO 28
<211> LENGTH: 44
<212> TYPE: DNA
<213> ORGANISM: Artificial
<220> FEATURE:
<223> OTHER INFORMATION: Primer

<400> SEQUENCE: 28
tgctaaatga caaacattcc aatgacagct cattagggtt cgat              44

<210> SEQ ID NO 29
<211> LENGTH: 17
<212> TYPE: DNA
<213> ORGANISM: Artificial
<220> FEATURE:
<223> OTHER INFORMATION: Primer

<400> SEQUENCE: 29 tggttcccctt atgacaa                                           17

```
<210> SEQ ID NO 30
<211> LENGTH: 19
<212> TYPE: DNA
<213> ORGANISM: Artificial
<220> FEATURE:
<223> OTHER INFORMATION: Primer

<400> SEQUENCE: 30
aaccattaaa gacaggagc                                                        19

<210> SEQ ID NO 31
<211> LENGTH: 18
<212> TYPE: DNA
<213> ORGANISM: Artificial
<220> FEATURE:
<223> OTHER INFORMATION: Primer

<400> SEQUENCE: 31
acgtacgttc tctctatc                                                         18

<210> SEQ ID NO 32
<211> LENGTH: 18
<212> TYPE: DNA
<213> ORGANISM: Artificial
<220> FEATURE:
<223> OTHER INFORMATION: Primer

<400> SEQUENCE: 32
actgattccc ctaaaatc                                                         18

<210> SEQ ID NO 33
<211> LENGTH: 17
<212> TYPE: DNA
<213> ORGANISM: Artificial
<220> FEATURE:
<223> OTHER INFORMATION: Primer

<400> SEQUENCE: 33
tcccgagtag ctgggcc                                                          17

<210> SEQ ID NO 34
<211> LENGTH: 17
<212> TYPE: DNA
<213> ORGANISM: Artificial
<220> FEATURE:
<223> OTHER INFORMATION: Primer

<400> SEQUENCE: 34
gtcgcgcgcc tgtaatc                                                          17

<210> SEQ ID NO 35
<211> LENGTH: 42
<212> TYPE: DNA
<213> ORGANISM: Artificial
<220> FEATURE:
<223> OTHER INFORMATION: Primer

<400> SEQUENCE: 35
gtgaaagccc gtctctagga tacaggcgcc cgccaccacg cc                              42

<210> SEQ ID NO 36
<211> LENGTH: 43
<212> TYPE: DNA
<213> ORGANISM: Artificial
<220> FEATURE:
<223> OTHER INFORMATION: Primer
```

<400> SEQUENCE: 36
ttagccggga tggtctggag ctccagcact ctgggaggcc gag    43

<210> SEQ ID NO 37
<211> LENGTH: 17
<212> TYPE: DNA
<213> ORGANISM: Artificial
<220> FEATURE:
<223> OTHER INFORMATION: Primer

<400> SEQUENCE: 37
atagaacaaa gtagccg    17

<210> SEQ ID NO 38
<211> LENGTH: 17
<212> TYPE: DNA
<213> ORGANISM: Artificial
<220> FEATURE:
<223> OTHER INFORMATION: Primer

<400> SEQUENCE: 38
tgacctcgtg atccacc    17

<210> SEQ ID NO 39
<211> LENGTH: 19
<212> TYPE: DNA
<213> ORGANISM: Artificial
<220> FEATURE:
<223> OTHER INFORMATION: Primer

<400> SEQUENCE: 39
gtgcctttac agatagcat    19

<210> SEQ ID NO 40
<211> LENGTH: 21
<212> TYPE: DNA
<213> ORGANISM: Artificial
<220> FEATURE:
<223> OTHER INFORMATION: Primer

<400> SEQUENCE: 40
gaaaaagtgt acgagttctt g    21

<210> SEQ ID NO 41
<211> LENGTH: 43
<212> TYPE: DNA
<213> ORGANISM: Artificial
<220> FEATURE:
<223> OTHER INFORMATION: Primer

<400> SEQUENCE: 41
gtttcataac cttcagcaag ctttccatac agtcatttca cgc    43

<210> SEQ ID NO 42
<211> LENGTH: 40
<212> TYPE: DNA
<213> ORGANISM: Artificial
<220> FEATURE:
<223> OTHER INFORMATION: Primer

<400> SEQUENCE: 42
gaggtcattg cagcttgctt acttcgatca ctggaccgcg    40

<210> SEQ ID NO 43

```
<211> LENGTH: 18
<212> TYPE: DNA
<213> ORGANISM: Artificial
<220> FEATURE:
<223> OTHER INFORMATION: Primer

<400> SEQUENCE: 43
aactcatagt ggccaaca                                                   18

<210> SEQ ID NO 44
<211> LENGTH: 21
<212> TYPE: DNA
<213> ORGANISM: Artificial
<220> FEATURE:
<223> OTHER INFORMATION: Primer

<400> SEQUENCE: 44
gtacctgtta tgaaagtgtt c                                               21

<210> SEQ ID NO 45
<211> LENGTH: 19
<212> TYPE: DNA
<213> ORGANISM: Artificial
<220> FEATURE:
<223> OTHER INFORMATION: Primer

<400> SEQUENCE: 45
gcatcgtggt gattgatga                                                  19

<210> SEQ ID NO 46
<211> LENGTH: 18
<212> TYPE: DNA
<213> ORGANISM: Artificial
<220> FEATURE:
<223> OTHER INFORMATION: Primer

<400> SEQUENCE: 46
ggttcgttgg caatactc                                                   18

<210> SEQ ID NO 47
<211> LENGTH: 38
<212> TYPE: DNA
<213> ORGANISM: Artificial
<220> FEATURE:
<223> OTHER INFORMATION: Primer

<400> SEQUENCE: 47
ctttcggctt gttgcccgcc tgctgtcggc tttaacct                              38

<210> SEQ ID NO 48
<211> LENGTH: 43
<212> TYPE: DNA
<213> ORGANISM: Artificial
<220> FEATURE:
<223> OTHER INFORMATION: Primer

<400> SEQUENCE: 48
agcgaagagg cagtcaacgt tttggttttt gtcacgcgct atc                       43

<210> SEQ ID NO 49
<211> LENGTH: 19
<212> TYPE: DNA
<213> ORGANISM: Artificial
<220> FEATURE:
<223> OTHER INFORMATION: Primer

<400> SEQUENCE: 49
```
tcgaaaccaa tgcctaaag                                                19

<210> SEQ ID NO 50
<211> LENGTH: 17
<212> TYPE: DNA
<213> ORGANISM: Artificial
<220> FEATURE:
<223> OTHER INFORMATION: Primer

<400> SEQUENCE: 50
gcgcacttac aggcgat                                                  17

<210> SEQ ID NO 51
<211> LENGTH: 17
<212> TYPE: DNA
<213> ORGANISM: Artificial
<220> FEATURE:
<223> OTHER INFORMATION: Primer

<400> SEQUENCE: 51
cccatctcac actcatg                                                  17

<210> SEQ ID NO 52
<211> LENGTH: 17
<212> TYPE: DNA
<213> ORGANISM: Artificial
<220> FEATURE:
<223> OTHER INFORMATION: Primer

<400> SEQUENCE: 52
tggccaaaac tgcagct                                                  17

<210> SEQ ID NO 53
<211> LENGTH: 39
<212> TYPE: DNA
<213> ORGANISM: Artificial
<220> FEATURE:
<223> OTHER INFORMATION: Primer

<400> SEQUENCE: 53
caagaacaac ccgtcccccc ttccacattc cacttagcg                          39

<210> SEQ ID NO 54
<211> LENGTH: 44
<212> TYPE: DNA
<213> ORGANISM: Artificial
<220> FEATURE:
<223> OTHER INFORMATION: Primer

<400> SEQUENCE: 54
taggaagccg ttttttatg ccccctgtag agaacattct tgtg                     44

<210> SEQ ID NO 55
<211> LENGTH: 18
<212> TYPE: DNA
<213> ORGANISM: Artificial
<220> FEATURE:
<223> OTHER INFORMATION: Primer

<400> SEQUENCE: 55
atagtaataa tgacttaa                                                 18

<210> SEQ ID NO 56
<211> LENGTH: 18
<212> TYPE: DNA

```
<213> ORGANISM: Artificial
<220> FEATURE:
<223> OTHER INFORMATION: Primer

<400> SEQUENCE: 56
catcctttca tatgttcc                                                18
```

NUCLEIC ACID EXTRACTION COMPOSITION, REAGENT AND KIT CONTAINING THE SAME AND USE THEREOF

CROSS REFERENCE TO RELATED APPLICATIONS

This application claims the priority of Chinese Patent Application No. 202010347016.5, filed on Apr. 28, 2020, and the disclosures of which are hereby incorporated by reference.

FIELD

The present disclosure relates to the field of biotechnology, in particular to a nucleic acid extraction composition, uses thereof, and reagents and kits containing the same.

BACKGROUND

Nucleic acid extraction is usually the first step to complete all molecular reactions. The quality of the completion of this step directly affects the success of subsequent biological reactions. Nucleic acid extraction and purification technology is a basic technology in molecular biology experiments. Nucleic acid extraction and purification are needed in experimental processes such as the target gene extraction, PCR product purification or gel extraction, and the extraction of plasmids in gene cloning. The nucleic acid separation and purification technology was originated in the 1950s. In the 1970s and 1980s, the traditional nucleic acid purification method by precipitation, dissolution and separation had been widely used and promoted.

Commonly used nucleic acid extraction and purification techniques include TRIzol™ method, spin-column method, magnetic bead method and other methods. The nucleic acid extraction reagents currently used for these methods all contain volatile organic solvents. In TRIzol™ method, proteins and nucleic acids are separated using the difference in the distribution of DNA, RNA, and protein in the organic layer and the aqueous layer. In the process of obtaining nucleic acid, phenol, chloroform, isoamyl alcohol, isopropanol, ethanol, etc. which are harmful to the health of operators, are used, and the extraction results of different samples are not reproducible. The steps of extracting nucleic acid by TRIzol™ are cumbersome, taking at least 1.5 h from sample lysis to obtaining nucleic acid. Due to the disadvantages of TRIzol™, such as harmness, tedious operation, time consuming and incompatibility with the chip, etc., it is not suitable for the use in clinical detection. In the conventional centrifugation adsorption column method and the magnetic bead method, ethanol or isopropanol is also needed for binding when extracting nucleic acid, and ethanol is needed to be added when washing is performed. For the nucleic acid extraction reagent, the step of adding ethanol makes the operation relatively complicated and time-consuming, and the reagents with ethanol cannot be stored for a long time. If the ethanol cannot be completely removed, it will participate in subsequent reactions. Moreover, the extraction and purification reagents containing ethanol are not suitable for use on microfluidic chips.

Therefore, there is a need to provide a set of extraction reagents without adding any volatile organic solvents and methods of use thereof to quickly and efficiently extract and purify nucleic acids in a variety of samples.

SUMMARY

In view of this, the present disclosure provides a nucleic acid extraction composition, reagent and kit containing the same, and uses thereof. The present disclosure provides a set of extraction reagents without adding any volatile organic solvents and methods of use thereof to quickly and efficiently extract and purify nucleic acids in a variety of samples.

In order to achieve the above-mentioned purpose of the present disclosure, the present disclosure provides the following technical solutions.

The present disclosure provides a nucleic acid extraction composition comprising a binding buffer and a wash buffer; wherein the binding buffer comprises a composition comprising glycogen, 3-(Morpholin-4-yl) propane-1-sulfonic acid (MOPS), polyamine and tris (2-carboxyethyl) phosphine (TCEP), the wash buffer comprises a composition comprising guanidine hydrochloride, potassium acetate, glycogen, MOPS and polyamine.

In some specific embodiments of the present disclosure, in the binding buffer, the concentration of glycogen is 0.1% to 1% (m/v), the concentration of MOPS is 10 mM to 20 mM, the concentration of polyamine is 0.1% to 2% (m/v), and the concentration of TCEP is 5 mM to 50 mM; the polyamine comprises spermine, spermidine, butanediamine or a mixture thereof.

The pH of the binding buffer is 8.5 to 10. Preferably, the pH of the solution is adjusted to 8.5 to 10 with sodium bisulfate.

In some specific embodiments of the present disclosure, in the wash buffer, the concentration of guanidine hydrochloride is 0.05 M to 0.6 M, the concentration of potassium acetate is 0.05 M to 0.5 M, the concentration of glycogen is 0.01% to 0.1% (m/v), the concentration of MOPS is 1 mM to 2 mM, and the concentration of polyamine is 0.01% to 0.3% (m/v); the polyamine comprises spermine, spermidine, butanediamine or a mixture thereof.

The pH of the wash buffer is 5 to 6. Preferably, the pH of the solution is adjusted to 5 to 6 with sodium bisulfate;

In some specific embodiments of the present disclosure, the nucleic acid extraction composition further comprises one or more of a lysis buffer, an enhancer, and an elution buffer.

The lysis buffer comprises guanidine isothiocyanate, TRITON™ X-100 (2-[4-(2,4,4-trimethylpentan-2-yl) phenoxy] ethanol) or a mixture thereof.

The enhancer comprises proteinase K, trehalose, calcium chloride or a mixture thereof.

The elution buffer comprises sodium hydroxide, 1×Tris-EDTA (TE) buffer or a mixture thereof.

In some specific embodiments of the present disclosure, in the lysis buffer, the concentration of guanidine isothiocyanate is 2 M to 8 M, the concentration of TRITON™ X-100 is 5% to 20% (v/v), and the pH value is 3 to 6.

In the enhancer, the concentration of proteinase K is 10 mg/ml to 25 mg/ml, the concentration of trehalose is 3% to 12% (m/v), and the concentration of calcium chloride is 5 mM to 20 mM.

The pH value of 1×TE buffer in the elution buffer is adjusted to 8 to 10 with sodium hydroxide.

On the basis of the above, the present disclosure also provides the use of the nucleic acid extraction composition in the preparation of a product for nucleic acid extraction and/or nucleic acid detection, wherein the product is a reagent and/or a kit.

On the basis of the above, the present disclosure provides a nucleic acid extraction reagent or nucleic acid detection reagent comprising the nucleic acid extraction composition and a reagent acceptable for detection.

The present disclosure also provides a nucleic acid extraction kit or nucleic acid detection kit comprising the nucleic acid extraction composition or the nucleic acid extraction reagent or nucleic acid detection reagent and a reagent or carrier acceptable for detection.

In some specific embodiments of the present disclosure, the carrier includes a silicon-based adsorption column, magnetic beads, glass beads, and a chitosan or silica modified carrier.

The present disclosure also provides a method of nucleic acid extraction or detection for non-diagnostic purposes, which comprises steps of mixing a sample to be tested with the nucleic acid extraction composition or the nucleic acid extraction reagent or nucleic acid detection reagent and performing extraction and/or detection.

The present disclosure provides a nucleic acid extraction and purification reagent free of volatile organic solvents to prevent the damage caused by volatile organic solvents to a human body, and also greatly improve the timeliness of nucleic acid extraction and purification, making the operations extremely simple, and by which the nucleic acid may be obtained within 10 minutes at the soonest, and the obtained nucleic acid may be used for biological reactions such as PCR, NASBA, LAMP and RPA. Moreover, the reagents of the present disclosure can be used for obtaining nucleic acids of cells, bacteria, fungi, DNA viruses and RNA viruses from various complex samples such as blood, throat swab preserving fluid, saliva, urine, sputum, excrement and the like, and is very suitable for clinical and scientific research application.

BRIEF DESCRIPTION OF DRAWINGS

In order to illustrate the examples of the present disclosure or the technical solutions in the prior art more clearly, the drawings that need to be used in the description of the examples or the prior art will be introduced briefly in the following.

DETAILED DESCRIPTION

Figure 1:
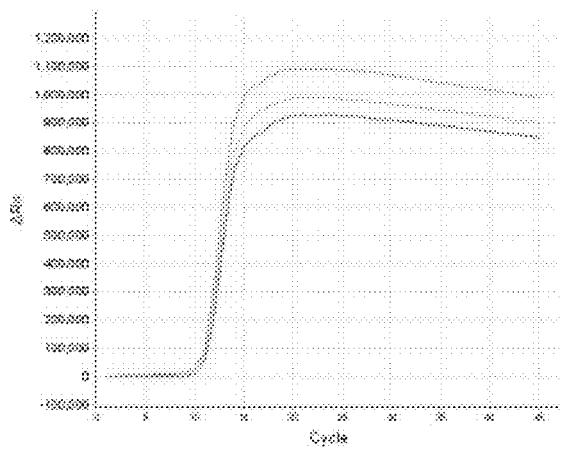
FIG. 1 shows the amplification results of Example 1, in which (A) shows the result from 1000 copies/μL sample; (B) shows the result from 100 copies/μL sample; (C) shows the result from 10 copies/μL sample; and (D) shows the result of 0 copies/μL sample.
Figure 1:
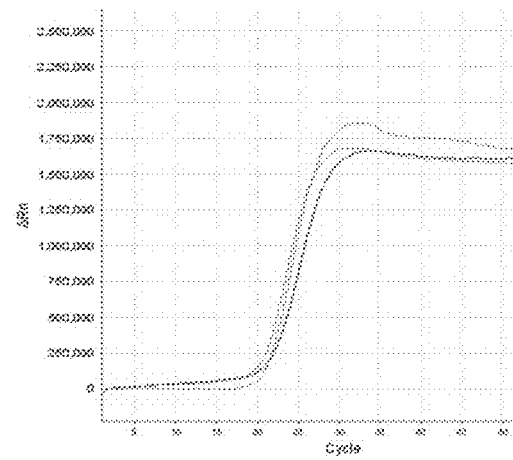
Figure 1:
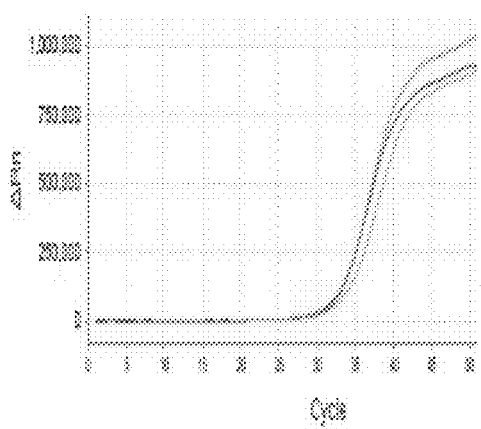
Figure 1:
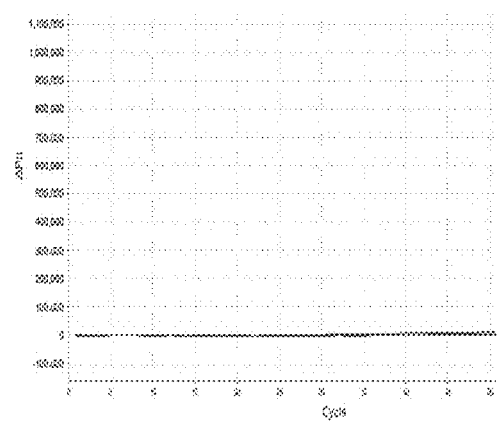

The present disclosure discloses a nucleic acid extraction composition, reagent and kit containing the same and uses thereof, which can be implemented by those skilled in the art by referring to this disclosure and appropriately improving process parameters. In particular, it should be pointed out that all similar substitutions and modifications are obvious to those skilled in the art, and they are all deemed to be included in the present disclosure. The methods and uses of the present disclosure have been described through the preferred examples, and for related personnel the methods and uses described herein can be modified or appropriately changed and combined to achieve and apply the technology of the present disclosure without departing from the disclosure, spirit and scope of the present disclosure.

The present disclosure has developed a set of nucleic acid extraction and purification reagents free of volatile organic solvents, which can be used with a variety of nucleic acid adsorption carriers, including a silicon-based adsorption column, magnetic beads, glass beads, and various chitosan or silica modified carriers.

The specific technical solution is as follows. The nucleic acid extraction composition comprises a binding buffer and a wash buffer, the components, concentration and pH of which have an important influence on the extraction result. The nucleic acid extraction reagents include a lysis buffer, an enhancer, a binding buffer, a wash buffer, and an elution buffer. The lysis buffer comprises guanidine isothiocyanate and TRITON™ X-100; the enhancer comprises proteinase K, trehalose, and calcium chloride; the binding buffer comprises glycogen, MOPS, polyamine, sodium bisulfate, and TCEP; the wash buffer comprises guanidine hydrochloride, potassium acetate, glycogen, MOPS, polyamine, and sodium bisulfate; and the elution buffer comprises sodium hydroxide and 1×TE buffer.

Further, in the lysis buffer, the concentration of guanidine isothiocyanate is 2 M to 8 M, the concentration of TRITON™ X-100 is 5% to 20% (v/v); and the pH of the solution is 3 to 6.

Further, in the enhancer, the concentration of proteinase K is 10 mg/ml to 25 mg/ml, the concentration of trehalose is 3% to 12% (m/v) and the concentration of calcium chloride is 5 mM to 20 mM.

Further, in the binding buffer, the concentration of glycogen is 0.1% to 1% (m/v), the concentration of MOPS is 10 mM to 20 mM, the concentration of polyamine is 0.1% to 2% (m/v), the concentration of TECP is 5 mM to 50 mM; the polyamine may comprise spermine, spermidine, and butanediamine; the pH of the solution is adjusted to 8.5 to 10 with sodium bisulfate.

Further, in the wash buffer, the concentration of guanidine hydrochloride is 0.05 M to 0.6 M, the concentration of potassium acetate is 0.05 M to 0.5 M, the concentration of glycogen is 0.01% to 0.1% (m/v), the concentration of MOPS is 1 mM to 2 mM, and the concentration of spermine or spermidine is 0.01% to 0.3% (m/v); the pH of the solution is adjusted to 5 to 6 with sodium bisulfate.

Further, the pH of 1×TE buffer in the elution buffer is adjusted to 8 to 10 with sodium hydroxide.

Adjustment of the concentrations of each component or pH, or replacement of some salt ions, such as replacing potassium acetate to salt ions such as sodium chloride and magnesium chloride, are all within the protection scope of the present disclosure, which are not limited hereby in the present disclosure.

The components of the extraction reagents provided by the present disclosure particularly comprise the components, concentration and pH of the binding buffer and the wash buffer; the reagents are used in a variety of nucleic acid adsorption carriers, including a silicon-based adsorption column, magnetic beads, glass beads, and various chitosan or silica modified carriers. The extraction and purification of bacteria or virus DNA and RNA from blood, urine, saliva, throat swab preserving fluid, sputum and other samples may be performed without using organic solvents in the whole process. The nucleic acid may be obtained within 10 minutes. Therefore, the present disclosure is of good value in scientific research and clinical application.

The present disclosure provides a nucleic acid extraction composition and uses thereof. The materials and reagents used in the nucleic acid extraction composition or the reagents and kits containing the same are all commercially available.

The present disclosure will be further illustrated in the following examples.

Example 1

The nucleic acid extraction reagents include the followings.

Lysis buffer: the concentration of guanidine isothiocyanate is 4 M, the concentration of TRITON™ X-100 is 20% (v/v), and the pH of the solution is 6.0.

Binding buffer: the concentration of glycogen is 0.5% (m/v), the concentration of MOPS is 20 mM, the concentration of spermine is 0.5% (m/v), the concentration of TECP is 6 mM, and pH is 9.5.

Wash buffer: the concentration of guanidine hydrochloride is 0.1 M, the concentration of potassium acetate is 0.15 M, the concentration of glycogen is 0.05% (m/v), the concentration of MOPS is 2 mM, the concentration of spermine is 0.2% (m/v), and pH is 6.0.

Enhancer: the concentration of proteinase K is 20 mg/ml, the concentration of trehalose is 6% (m/v), and the concentration of calcium chloride is 5 mM.

Elution buffer: 1×TE buffer with pH of 10.0.

Method: EV71 pseudovirus (constructed by Zeesan Biotech, Xiamen, China) was diluted with saliva (from a healthy employee of CapitalBio Corporation) so that the concentration of the pseudovirus in the saliva was 1000 copies/μL, 100 copies/μL, 10 copies/μL or 0 copies/μL, respectively, for later use. 200 μL of lysis buffer, 400 μL of binding buffer and 20 μL of enhancer were added to 200 μL of virus sample of each concentration and mixed well, leaving it stand for 8 min at room temperature. All the resulting liquid was transferred to the spin column and centrifugation was performed at 13,000 rpm for 1 min, then the waste liquid was discarded. 200 μL of wash buffer was added to the spin column and centrifugation was performed at 13,000 rpm for 1 min. This step was repeated once. The spin column was transferred to a nucleic acid collection tube, into which 50 μL of elution buffer was added and centrifugation was performed at 13,000 rpm for 1 min. The recovered nucleic acid was amplified using the RT-LAMP kit (Eiken Co., Ltd.) for RT-LAMP detection. The amplification system was as follows: 5 μL of 2×Buffer, 1.09 μL of primers, 0.24 μL of EvaGreen dye, 1.2 μL of Enzyme Mix, 0.47 μL of water, 2 μL of the extracted and purified nucleic acid. The detection program is 65° C. for 60 min.

The sequences of EV71 primers are as follows:

```
EV71-F3:
TGCGAGTGCTTATCAATGGT (as shown in SEQ ID NO: 1);

EV71-B3:
AGTTCTGGTTACGCATCGG (as shown in SEQ ID NO: 2);

EV71-FIP:
ACTGAGAACGTGCCCATCATGTATCCCACATTCGGAGAACAC (as
shown in SEQ ID NO: 3);

EV71-BIP:
CTGTGGGGACCTCCAAGTCCAAGGTATCCACGCCCTGAC (as
shown in SEQ ID NO: 4);

EV71-Lf:
CGTATTCAAGATCTTTCTCCTGTTT (as shown in SEQ ID
NO: 5);

EV71-Lb:
AGTACCCTTTAGTGGTTAGGATT (as shown in SEQ ID
NO: 6).
```

The amplification results are shown in FIG. 1, (A)-(D).

Example 2

Lysis buffer: the concentration of guanidine isothiocyanate is 6 M, the concentration of TRITON™ X-100 is 20% (v/v), and the pH of the solution is 6.0.

Binding buffer: the concentration of glycogen of 0.1% (m/v), the concentration of MOPS is 20 mM, the concentration of spermine is 0.1% (m/v), the concentration of TECP is 10 mM, and pH is 9.6.

Wash buffer: the concentration of guanidine hydrochloride is 0.05 M, the concentration of potassium acetate is 0.05 M, the concentration of glycogen is 0.01% (m/v), the concentration of MOPS is 1 mM, the concentration of spermine is 0.01% (m/v), and pH is 6.0.

Enhancer: the concentration of proteinase K is 20 mg/ml, the concentration of trehalose is 6% (m/v), and the concentration of calcium chloride is 5 mM.

Elution buffer: 1×TE buffer with pH of 10.0.

Method: EV71 pseudovirus (constructed by Zeesan Biotech, Xiamen, China) was diluted with saliva (from a healthy employee of CapitalBio Corporation) so that the concentration of the pseudovirus in the saliva was 1000 copies/μL, 100 copies/μL, 10 copies/μL or 0 copies/μL, respectively, for later use. 200 μL of lysis buffer, 400 μL of binding buffer and 20 μL of enhancer were added to 200 μL of virus sample of each concentration and mixed well, leaving it stand for 8 min at room temperature. All the liquid was transferred to the spin column and centrifugation was performed at 13,000 rpm for 1 min, then the waste liquid was discarded. 200 μL of wash buffer was added to the spin column and centrifugation was performed at 13,000 rpm for 1 min. This step was repeated once. The spin column was transferred to a nucleic acid collection tube, into which 50 μL of elution buffer was added and centrifugation was performed at 13,000 rpm for 1 min. The recovered nucleic acid was amplified using the RT-LAMP kit from Eiken Co., Ltd. for RT-LAMP detection. The amplification system was as follows: 5 μL of 2×Buffer, 1.09 μL of primers, 0.24 μL of EvaGreen dye, 1.2 μL of Enzyme Mix, 0.47 μL of water, 2 μL of the extracted and purified nucleic acid. The detection program was 65° C. for 60 min.

The sequences of EV71 primers are as follows:

```
EV71-F3:
TGCGAGTGCTTATCAATGGT (as shown in SEQ ID NO: 7);

EV71-B3:
AGTTCTGGTTACGCATCGG (as shown in SEQ ID NO: 8);

EV71-FIP:
ACTGAGAACGTGCCCATCATGTATCCCACATTCGGAGAACAC (as
shown in SEQ ID NO: 9);

EV71-BIP:
CTGTGGGGACCTCCAAGTCCAAGGTATCCACGCCCTGAC (as
shown in SEQ ID NO: 10);

EV71-Lf:
CGTATTCAAGATCTTTCTCCTGTTT (as shown in SEQ ID
NO: 11);
and

EV71-Lb:
AGTACCCTTTAGTGGTTAGGATT (as shown in SEQ ID
NO: 12).
```

Figure 2:
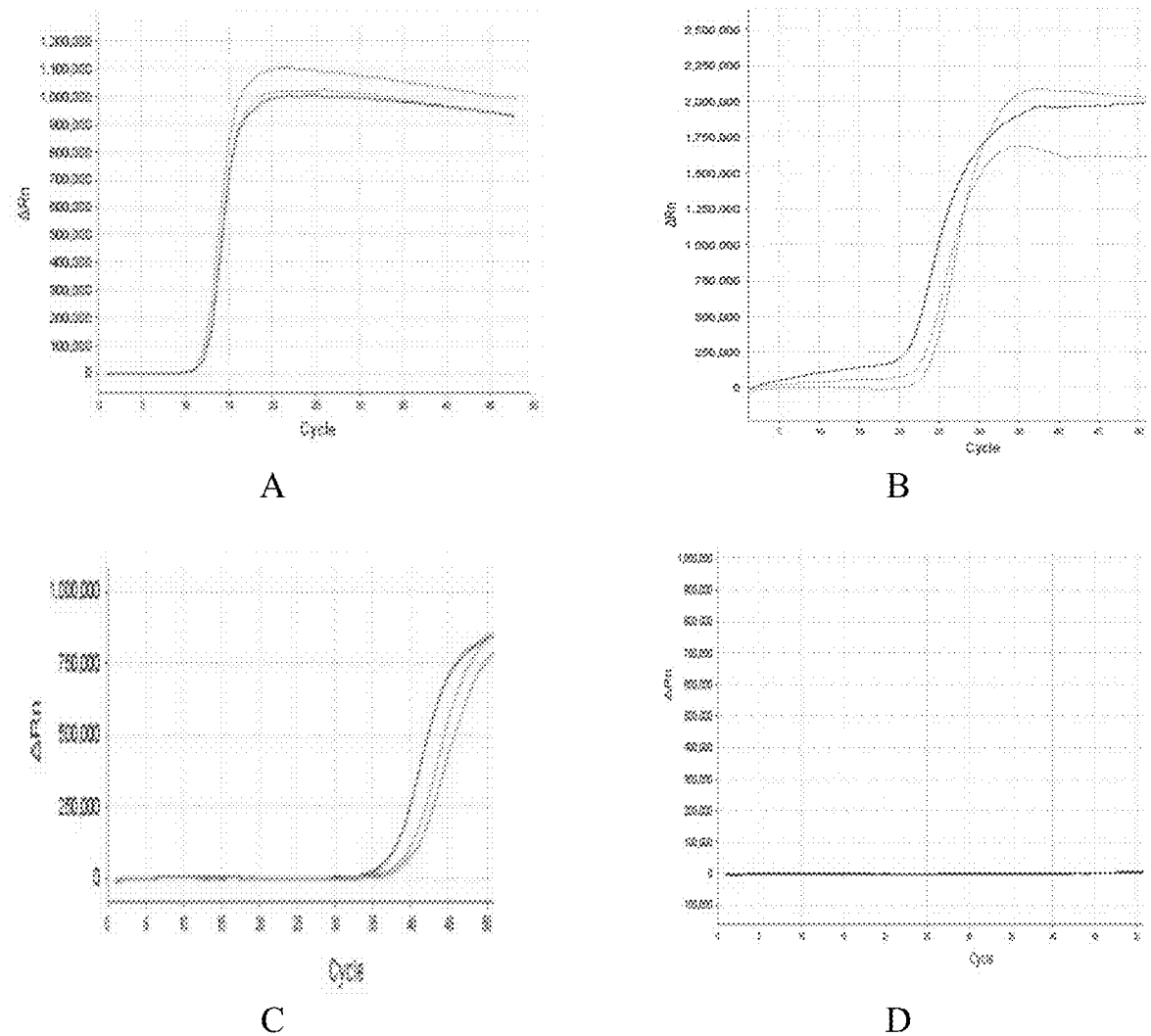
FIG. 2 shows the amplification results of Example 2, in which (A) shows the result from 1000 copies/μL sample; (B) shows the result from 100 copies/μL sample; (C) shows the result from 10 copies/μL sample; and (D) shows the result from 0 copies/μL sample.

The amplification results are shown in FIG. 2, (A)-(D).

Example 3

Lysis buffer: the concentration of guanidine isothiocyanate is 6 M, the concentration of TRITON™ X-100 is 5% (v/v), and the pH of the solution is 6.0.

Binding buffer: the concentration of glycogen is 1% (m/v), the concentration of MOPS is 20 mM, the concentration of spermine is 2% (m/v), the concentration of TECP is 10 mM, and pH is 9.6.

Wash buffer: the concentration of guanidine hydrochloride is 0.6 M, the concentration of potassium acetate is 0.5 M, the concentration of glycogen is 0.1% (m/v), the concentration of MOPS is 2 mM, the concentration of spermine is 0.3% (m/v), and pH is 5.0.

Enhancer: the concentration of proteinase K is 20 mg/ml, the concentration of trehalose is 6% (m/v), and the concentration of calcium chloride is 5 mM.

Elution buffer: 1×TE buffer with pH of 10.0.

Method: EV71 pseudovirus constructed by Zeesan Biotech, Xiamen, China was diluted with saliva (from a healthy employee of CapitalBio Corporation) so that the concentration of the pseudovirus in the saliva was 1000 copies/μL, 100 copies/μL, 10 copies/μL or 0 copies/μL, respectively, for later use. 200 μL of lysis buffer, 400 μL of binding buffer and 20 μL of enhancer were added to 200 μL of virus sample of each concentration and mixed well, leaving it stand for 8 min at room temperature. All the liquid was transferred to the spin column and centrifugation was performed at 13,000 rpm for 1 min, then the waste liquid was discarded. 200 μL of wash buffer was added to the spin column and centrifugation was performed at 13,000 rpm for 1 min. This step was repeated once. The spin column was transferred to a nucleic acid collection tube, into which 50 μL of elution buffer was added and centrifugation was performed at 13,000 rpm for 1 min. The recovered nucleic acid was amplified using the RT-LAMP kit from Eiken Co., Ltd. for RT-LAMP detection. The amplification system was as follows: 5 μL of 2×Buffer, 1.09 μL of primers, 0.24 μL of EvaGreen dye, 1.2 μL of Enzyme Mix, 0.47 μL of water, 2 μL of the extracted and purified nucleic acid. The detection program was 65° C. for 60 min.

The sequences of EV71 primers are as follows:

```
EV71-F3:
TGCGAGTGCTTATCAATGGT (as shown in SEQ ID NO: 13);

EV71-B3:
AGTTCTGGTTACGCATCGG (as shown in SEQ ID NO: 14);

EV71-FIP:
ACTGAGAACGTGCCCATCATGTATCCCACATTCGGAGAACAC (as
shown in SEQ ID NO: 15);

EV71-BIP:
CTGTGGGGACCTCCAAGTCCAAGGTATCCACGCCCTGAC (as
shown in SEQ ID NO: 16);

EV71-Lf:
CGTATTCAAGATCTTTCTCCTGTTT (as shown in SEQ ID
NO: 17);
and

EV71-Lb:
AGTACCCTTTAGTGGTTAGGATT (as shown in SEQ ID
NO: 18).
```

Figure 3:
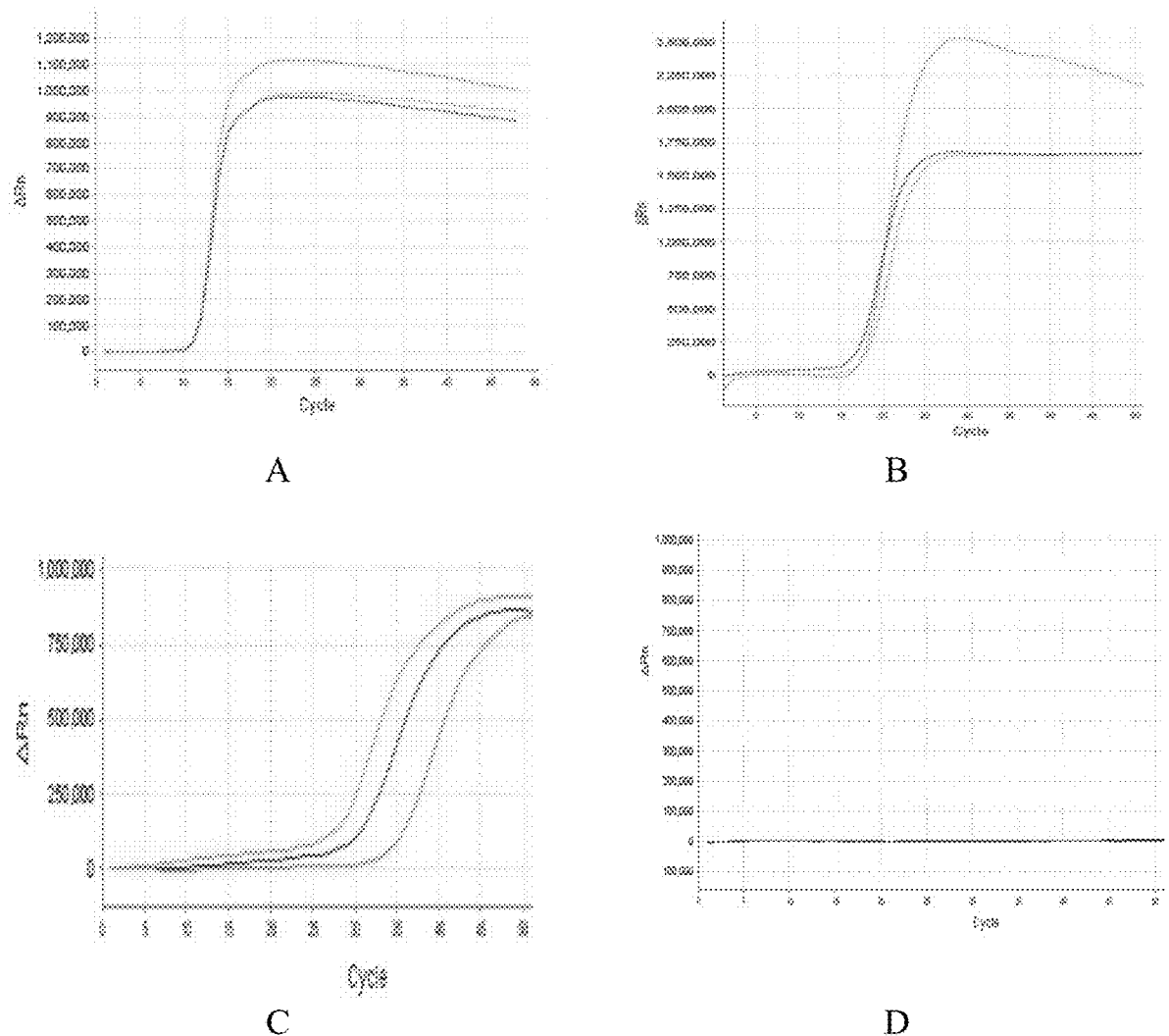
FIG. 3 shows the amplification results of Example 3, in which (A) shows the result from 1000 copies/μL sample; (B) shows the result from 100 copies/μL sample; (C) shows the result from 10 copies/μL sample; and (D) shows the result from 0 copies/μL sample.

The amplification results are shown in FIG. 3, (A)-(D).

Example 4

Amplification of RNA Extracted from Various Samples
The reagents used are as follows.

Lysis buffer: the concentration of guanidine thiocyanate is 4 M, the concentration of TRITON™ X-100 is 20% (v/v), and the pH of the solution is 6.0.

Binding buffer: the concentration of glycogen is 0.5% (m/v), the concentration of MOPS is 10 mM, the concentration of spermine is 0.1% (m/v), the concentration of TECP is 6 mM, and pH is 9.5.

Wash buffer: the concentration of guanidine hydrochloride is 0.05 M, the concentration of potassium acetate is 0.15 M, the concentration of glycogen is 0.01% (m/v), the concentration of MOPS is 1 mM; the concentration of spermine is 0.01% (m/v), and pH is 6.0.

Elution buffer: 1×TE buffer with pH of 10.

Enhancer: the concentration of proteinase K is 20 mg/ml, the concentration of trehalose is 6% (m/v), and the concentration of calcium chloride is 5 mM.

In order to assess the differences in the extraction ability of the nucleic acid extraction reagents on different samples, a saliva sample and an urine sample were selected. EV71 armored RNA was used as a quality control, and the RT-LAMP amplification reagents (Eiken Co., Ltd.) was used as detection reagents. Specifically, the amplification system was as follows: 5 µL of 2×Buffer, 1.09 µL of primers, 0.24 µL of EvaGreen dye, 1.2 µL of Enzyme Mix, 0.47 µL of water, and 2 µL of the extracted and purified nucleic acid.

Figure 4:
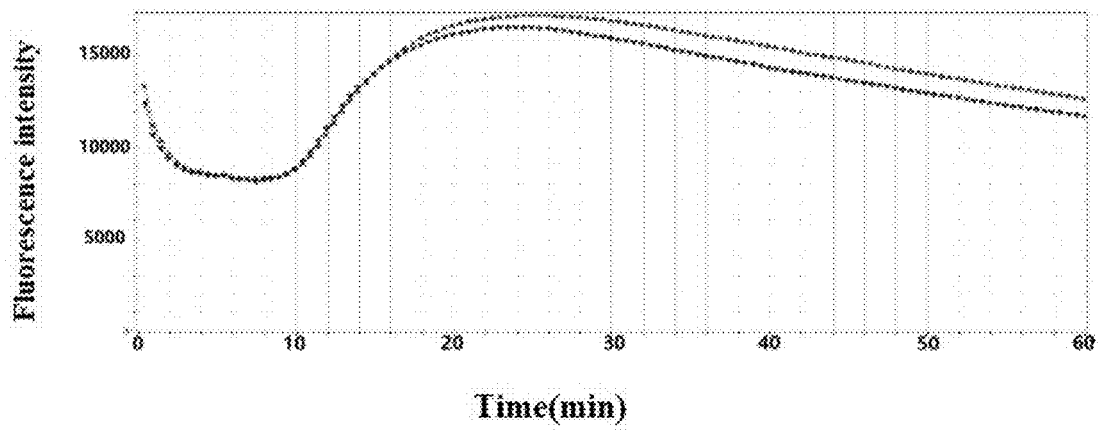
FIG. 4 shows the amplification results of Example 4, in which (A) shows the result of the RT-LAMP amplification of EV71 armored RNA (104 copies) in the saliva sample after extraction; and (B) shows the result of the RT-LAMP amplification of EV71 armored RNA (104 copies) in the urine sample after extraction.
Figure 4:
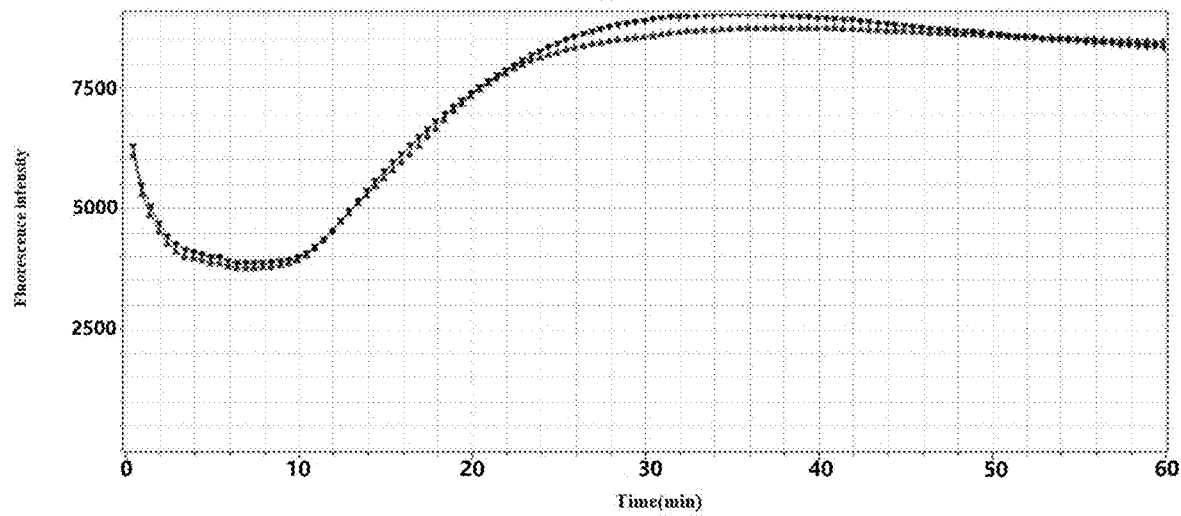

2 µL ($10^6$ copies/µL) of EV71 armored RNA was respectively added to 198 µL of the saliva sample and 198 µL of the urine sample to make the concentration of the armored RNA in the sample as 104 copies/µL. 200 µL of lysis buffer, 400 µL of binding buffer, and 20 µL of enhancer were added to each tube, mixed and heated at 55° C. for 15 minutes. All the lysed liquid was transferred to a adsorption column, and centrifugation was performed at 13,000 rpm for 40 s. The adsorption column was transferred to a new waste liquid collection tube, into which 200 µL of wash buffer was added, and centrifugation was performed at 13,000 rpm for 40 s. Washing was performed twice, then the waste liquid collection tube was replaced by a nucleic acid collection tube. 50 µL of elution buffer was added to the adsorption column, and centrifugation was performed at 13,000 rpm for 40 s. The adsorption column was discarded, and nucleic acid was recovered. 2 µL of the recovered nucleic acid was mixed with the RT-LAMP amplification reagents from Eiken Co., Ltd. (5 µL of 2×Buffer, 1.09 µL of primers, 0.24 µL of EvaGreen dye, 1.2 µL of Enzyme Mix, and 0.47 µL of water) and amplified at 65° C. for 60 min. The amplification results show that there is no significant difference in the recovery of nucleic acids from saliva and urine samples when using the extraction reagents of the present disclosure. The results are shown in FIG. 4, (A)-(B).

Example 5

Extraction of Viral Nucleic Acid at Different Concentrations

The reagents used are as follows.

Lysis buffer: the concentration of guanidine thiocyanate is 4 M, the concentration of TRITON™ X-100 is 20% (v/v), and the pH of the solution is 6.0.

Binding buffer: the concentration of glycogen of 1% (m/v), the concentration of MOPS is 20 mM, the concentration of spermine of 0.5% (m/v), the concentration of TECP is 20 mM, and pH is 9.5.

Wash buffer: the concentration of guanidine hydrochloride is 0.6 M, the concentration of potassium acetate is 0.5 M, the concentration of glycogen is 1% (m/v), the concentration of MOPS is 1 mM, the concentration of spermine is 0.3% (m/v), and pH is 6.0.

Elution buffer: 1×TE buffer with pH of 10.

Enhancer: the concentration of proteinase K is 20 mg/ml, the concentration of trehalose is 6% (m/v), and the concentration of calcium chloride is 5 mM.

In order to assess the extraction effect of the nucleic acid extraction reagents on samples with different viral loads, duck plague virus was selected as a standard quality control, and a saliva sample was used as a test sample. 198 µL of the saliva sample from the same tube was added to 3 of 1.5 mL EP tubes, respectively, into which 2 µL of duck plague virus of different concentrations was added to make the concentration of duck plague virus in the three tubes of saliva samples 1000 copies/µL, 100 copies/µL or 10 copies/µL, respectively. 200 µL of lysis buffer, 400 µL of binding buffer, and 20 µL of enhancer were added to the three tubes, mixed and heated at 55° C. for 15 minutes. All the lysed liquid was transferred to a adsorption column, and centrifugation was performed at 13,000 rpm for 40 s. The adsorption column was transferred to a new waste liquid collection tube, into which 200 µL of wash buffer was added, and centrifugation was performed at 13,000 rpm for 40 s. Washing was performed twice, then the waste liquid collection tube was replaced by a nucleic acid collection tube. 50 µL of elution buffer was added to the adsorption column, and centrifugation was performed at 13,000 rpm for 40 s. The adsorption column was discarded, and nucleic acid was recovered. The recovered nucleic acid was mixed with the reagents for LAMP and amplified at 65° C. for 60 min. The amplification results show that the nucleic acid extraction reagents can extract nucleic acids from samples with low viral load.

TABLE 1

Primer sequences for duck plague virus

| | | |
|---|---|---|
| YW-ART1-F3 | SEQ ID NO: 19 | ACATACCAAGTTATGCAGATGA |
| YW-ART1-B3 | SEQ ID NO: 20 | CCTCCGAACGATATGCTTC |
| YW-ART1-FIP | SEQ ID NO: 21 | CTACCTCTTGACCCTGATTATTTGTAAGCTTAGATTATCTAGTTTGTGGGAACAG |
| YW-ART1-BIP | SEQ ID NO: 22 | ACTCTAATAGCGCAATAACTCTCCTGAATTCTTACCACAAACCCCAAGC |
| YW-ART1-LF | SEQ ID NO: 23 | CATCTTGAAACAACGCACTAGTTC |
| YW-ART1-BF | SEQ ID NO: 24 | TTTTTTCTCTGTATTGCGTGTACGG |

Figure 5:
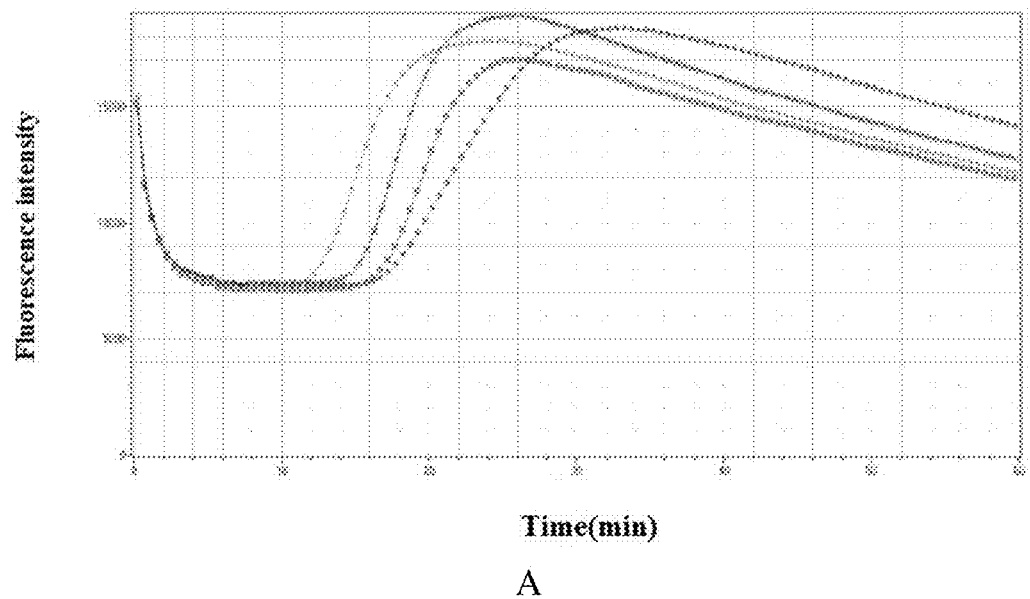
FIG. 5 shows the amplification results of Example 5, in which (A) shows the result at 1000 copies/μL of DPV (duck plague virus) contained in the saliva sample; (B) shows the result at 100 copies/μL of DPV contained in the saliva sample; and (C) shows the result at 10 copies/μL of DPV contained in the saliva sample.
Figure 5:
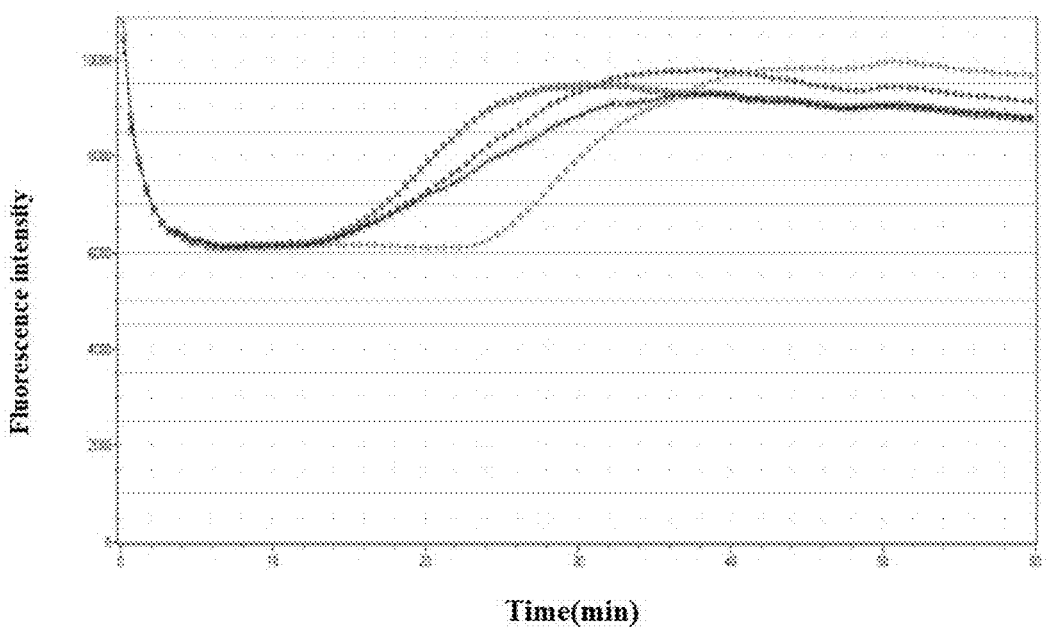
Figure 5:
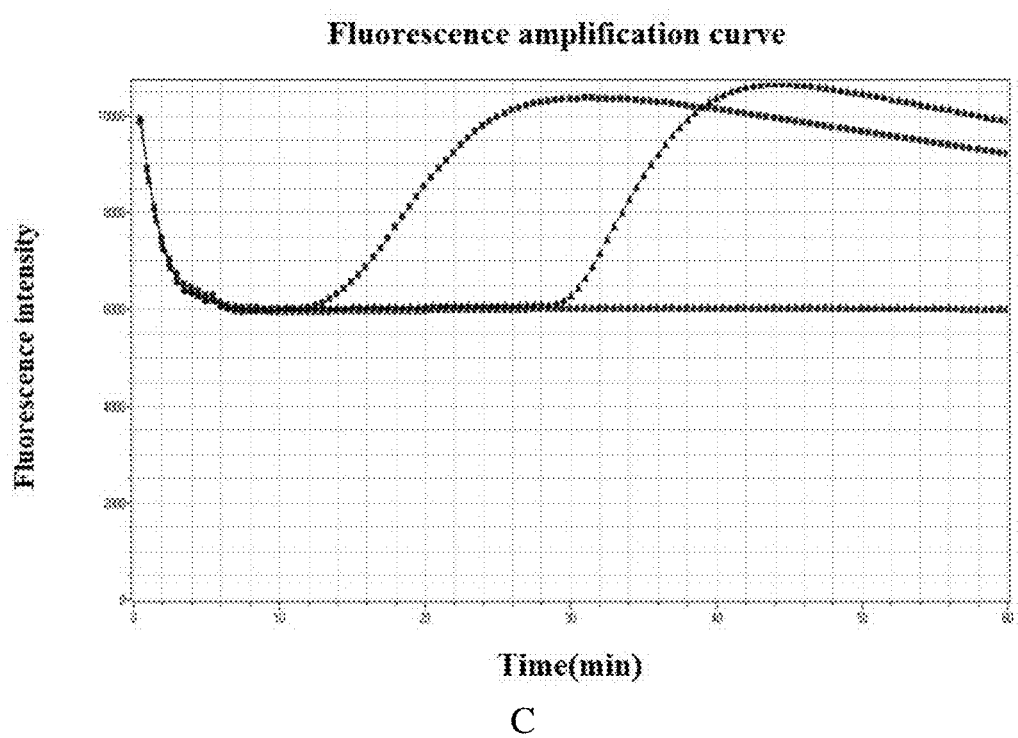

The results are shown in FIG. 5, (A)-(C).

Example 6

Nucleic Acid Extraction from Cell Samples

The reagents used are as follows.

Lysis buffer: the concentration of guanidine thiocyanate is 5 M, the concentration of TRITON™ X-100 is 4% (v/v), and the pH of the solution is 6.0.

Binding buffer: the concentration of glycogen is 1% (m/v), the concentration of MOPS is 20 mM, the concentration of spermine is 1% (m/v), the concentration of TECP is 10 mM, and pH is 9.0.

Wash buffer: the concentration of guanidine hydrochloride is 0.6 M, the concentration of potassium acetate is 0.5 M, the concentration of glycogen is 0.1% (m/v), the concentration of MOPS is 2 mM; the concentration of spermine is 0.3% (m/v), and pH is 5.0.

Enhancer: the concentration of proteinase K is 20 mg/ml, the concentration of trehalose is 6% (m/v), and the concentration of calcium chloride is 5 mM.

Elution buffer: 1×TE buffer with pH of 9.0.

Figure 6:
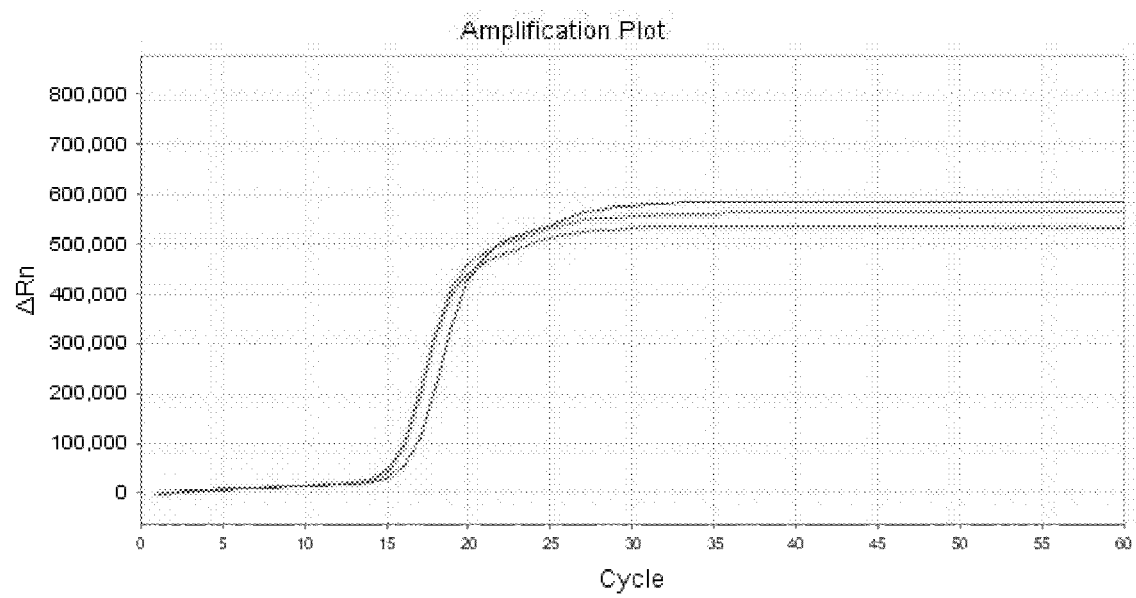
FIG. 6 shows the amplification results of Example 6, in which (A) shows the result from 1E4 copies/μL sample; (B) shows the result from 1E3 copies/μL sample; (C) shows the result from 1E2 copies/μL sample; and (D) shows the result from 1E1 copies/μL sample.
Figure 6:
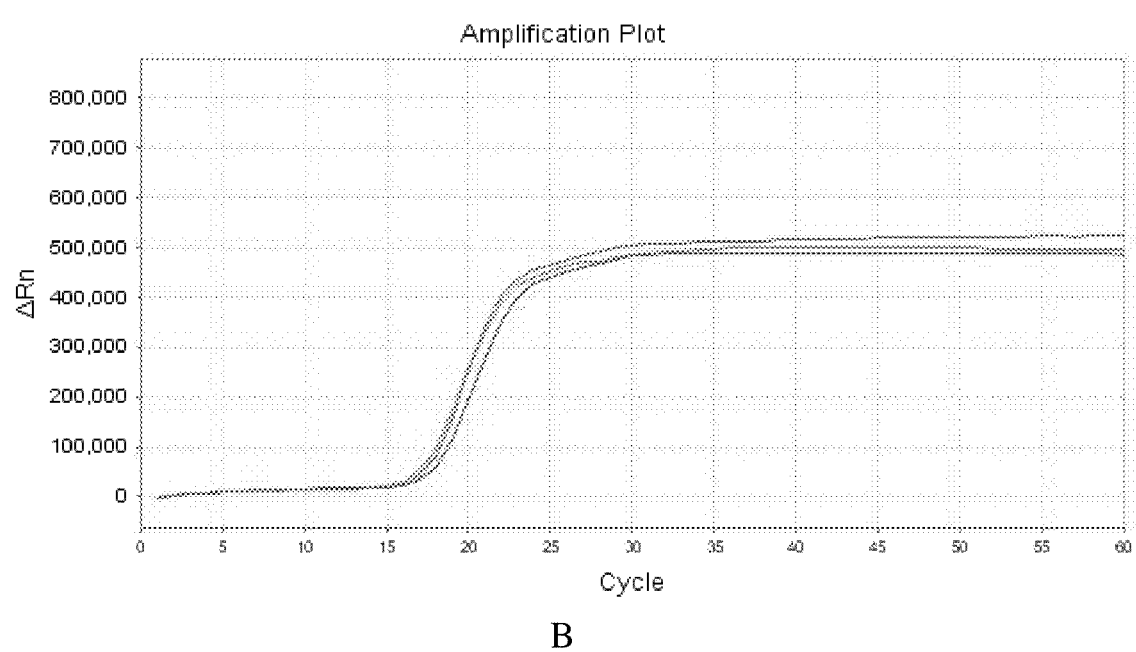
Figure 6:
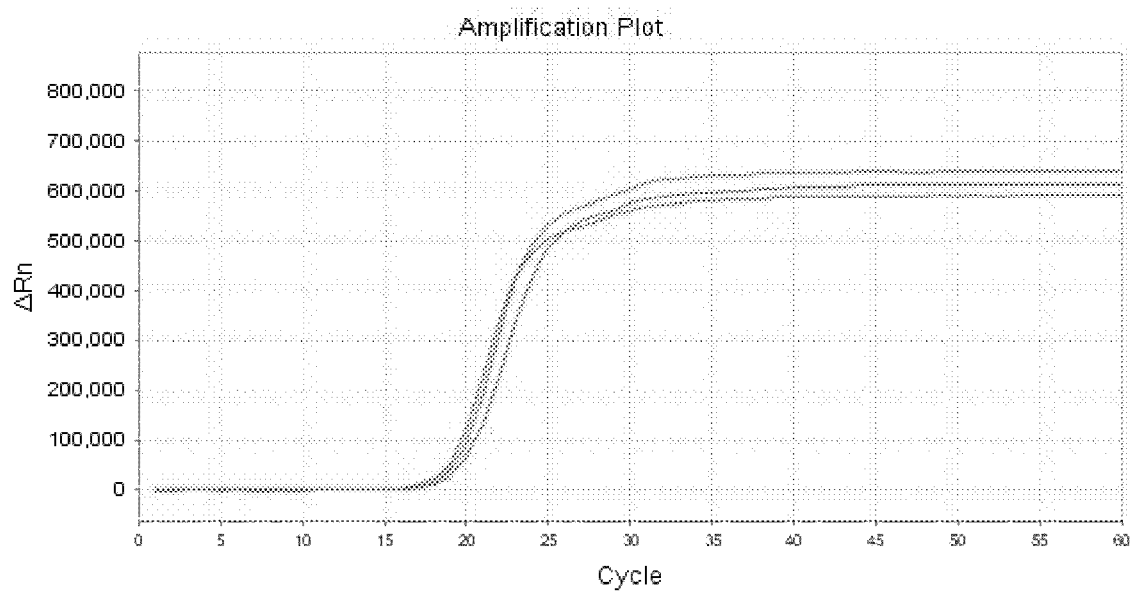
Figure 6:
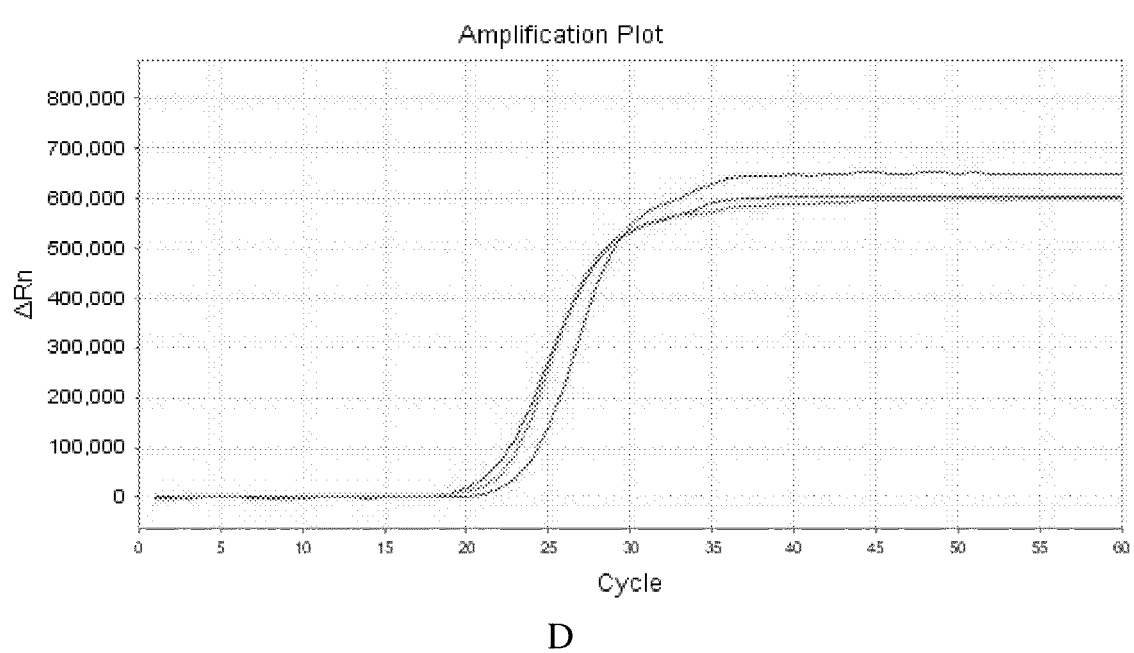

In order to verify the extraction and purification effect of the extraction reagents on cell nucleic acid, Hela cells were used as a sample to be extracted. 200 μL of cell samples, containing 1E4 copy/μL, 1E3 copy/μL, 1E2 copy/μL, and 1E1 copy/μL cells, were prepared respectively. 200 μL of lysis buffer, 400 μL of binding buffer, and 20 μL of enhancer were added to each tube, mixed and heated at 55° C. for 15 minutes. All the lysed liquid was transferred to an adsorption column, and centrifugation was performed at 13,000 rpm for 40 s. The adsorption column was transferred to a new waste liquid collection tube, into which 200 μL of wash buffer was added, and centrifugation was performed at 13,000 rpm for 40 s. Washing was performed twice, then the waste liquid collection tube was replaced by a nucleic acid collection tube. 50 μL of elution buffer was added to the adsorption column, and centrifugation was performed at 13,000 rpm for 40 s. The adsorption column was discarded, and nucleic acid was recovered. 2 μL of the recovered nucleic acid was mixed with the RT-LAMP amplification reagents from Eiken Co., Ltd. (5 μL of 2×Buffer, 1.09 μL of primers, 0.24 μL of EvaGreen dye, 1.2 μL of Enzyme Mix, and 0.47 μL of water) and amplified at 65° C. for 60 min. The amplification results show that target sequences can be amplified from all four nucleic acid samples extracted from cells (FIG. 6, (A)-(D)).

Primers for amplification are shown in Table 2.

TABLE 2

| Primer | Sequence | SEQ ID NO: |
|---|---|---|
| IC-4-F3 | TCCCGAGTAGCTGGGCC | 33 |
| IC-4-B3 | GTCGCGCGCCTGTAATC | 34 |
| IC-4-FIP | GTGAAAGCCCGTCTCTAGGATACAGGCGCCCGCCACCACGCC | 35 |
| IC-4-BIP | TTAGCCGGGATGGTCTGGAGCTCCAGCACTCTGGGAGGCCGAG | 36 |
| IC-4-LF | ATAGAACAAAGTAGCCG | 37 |
| IC-4-LB | TGACCTCGTGATCCACC | 38 |

Example 7

Nucleic Acid Extraction from Galanz Positive Bacteria

The reagents used are as follows.

Lysis buffer: the concentration of guanidine thiocyanate is 6 M, the concentration of TRITON™ X-100 is 5% (v/v), and the pH of the solution is 6.0.

Binding buffer: the concentration of glycogen is 1% (m/v), the concentration of MOPS is 20 mM, the concentration of spermine is 1.5% (m/v), the concentration of TECP is 10 mM, and pH is 9.7.

Wash buffer: the concentration of guanidine hydrochloride is 0.6 M, the concentration of potassium acetate is 0.5 M, the concentration of glycogen is 0.1% (m/v), the concentration of MOPS is 2 mM; the concentration of spermine is 0.3% (m/v), and pH is 5.0.

Enhancer: the concentration of proteinase K is 20 mg/ml, the concentration of trehalose is 6% (m/v), and the concentration of calcium chloride is 5 mM.

Elution buffer: 1×TE buffer with pH of 10.0.

Figure 7:
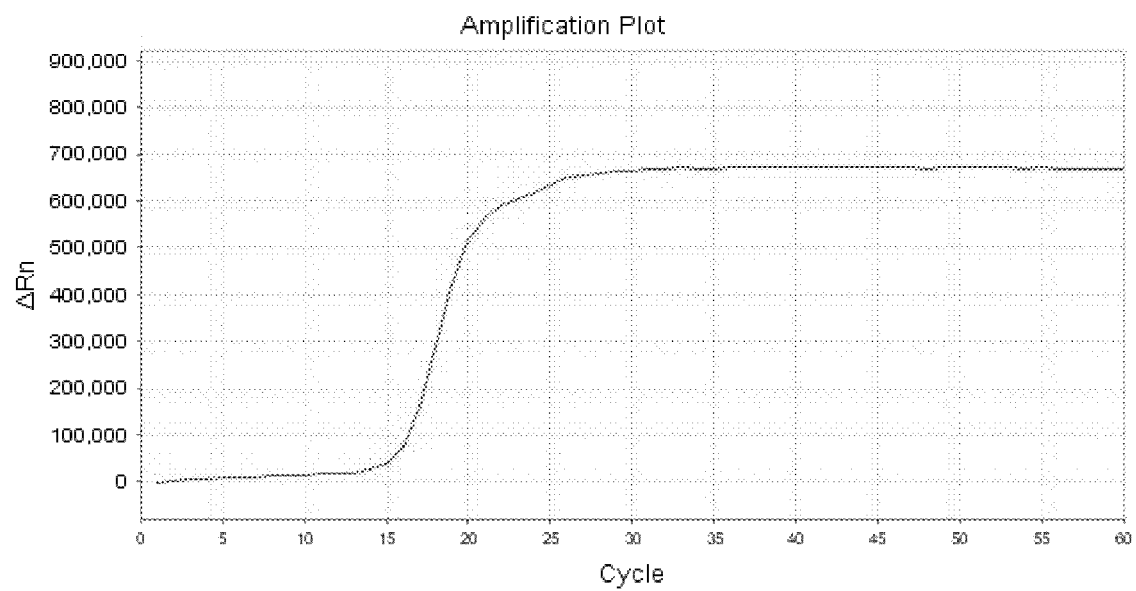
FIG. 7 shows the amplification results of Example 7, in which (A) shows the result from 1E4 copies/μL sample; (B) shows the result from 1E3 copies/μL sample; (C) shows the result from 1E2 copies/μL sample; and (D) shows the result from 1E1 copies/μL sample.
Figure 7:
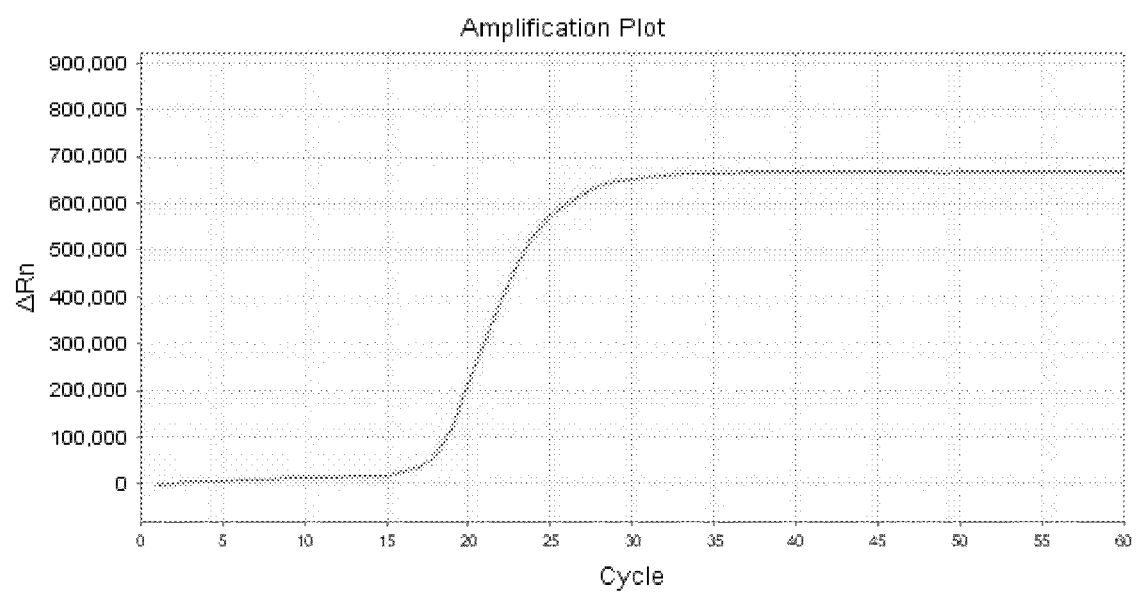
Figure 7:
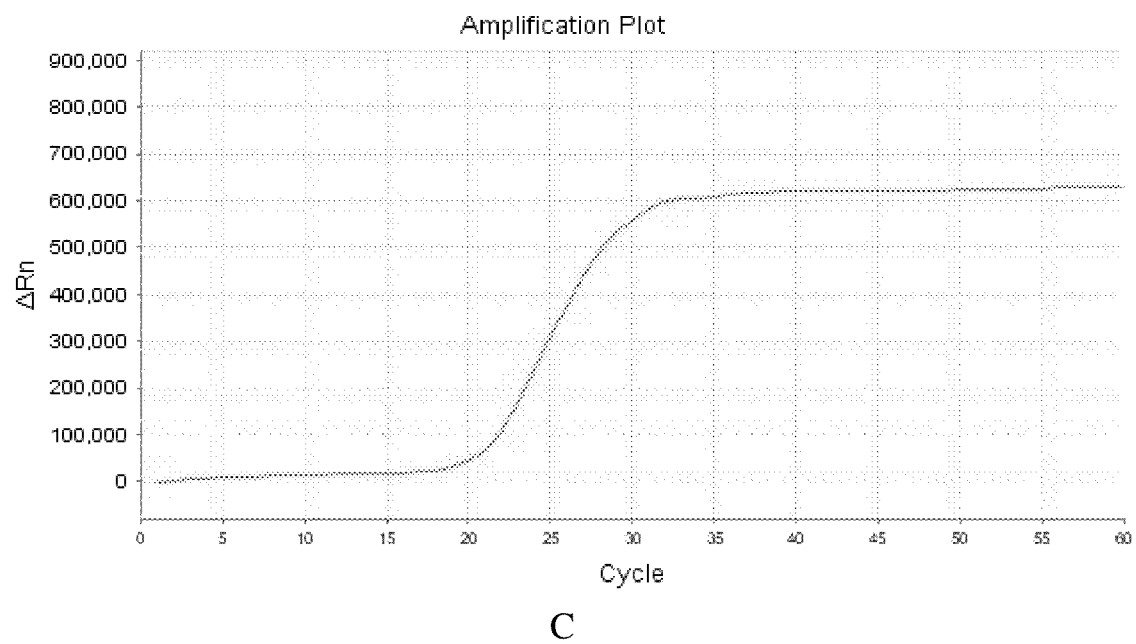
Figure 7:
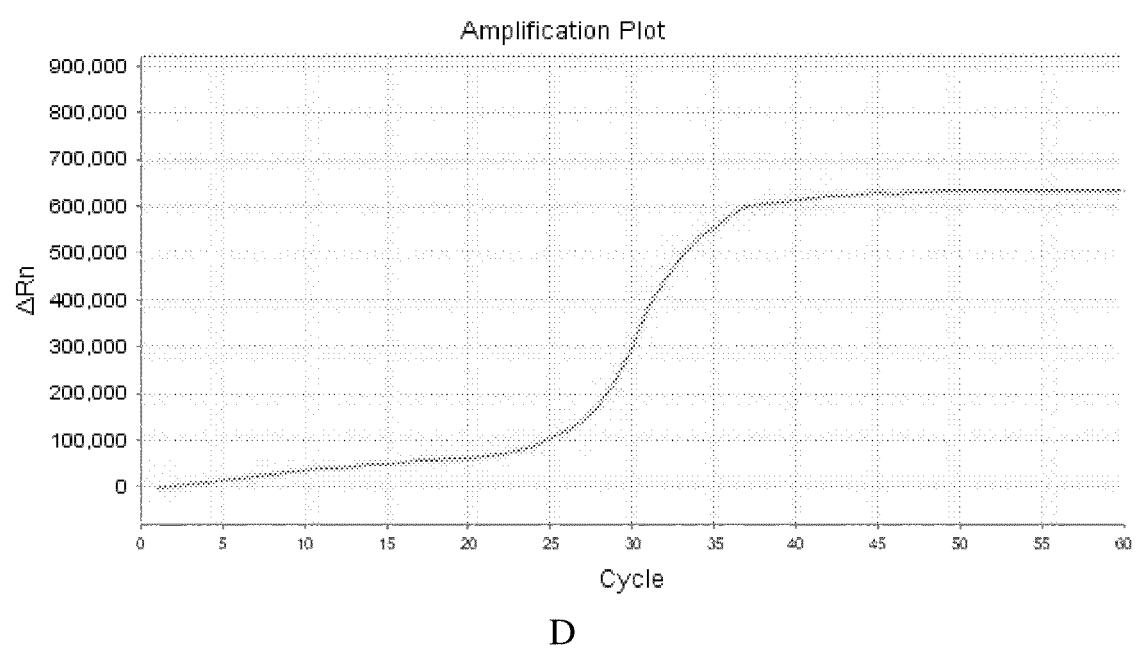

In order to verify the nucleic acid extraction and purification effect of the extraction reagents on Galanz positive bacteria samples, *Staphylococcus aureus* cells were used as the sample to be extracted. 200 µL of cell samples, containing 1E4 copy/µL, 1E3 copy/µL, 1E2 copy/µL and 1E1 copy/µL, were prepared respectively. 200 µL of lysis buffer, 400 µL of binding buffer, and 20 µL of enhancer were added to each tube, mixed and heated at 55° C. for 15 minutes. All the lysed liquid was transferred to an adsorption column, and centrifugation was performed at 13,000 rpm for 40 s. The adsorption column was transferred to a new waste liquid collection tube, into which 200 µL of wash buffer was added, and centrifugation was performed at 13,000 rpm for 40 s. Washing was performed twice, then the waste liquid collection tube was replaced by a nucleic acid collection tube. 50 µL of elution buffer was added to the adsorption column, and centrifugation was performed at 13,000 rpm for 40 s. The adsorption column was discarded, and nucleic acid was recovered. 2 µL of the recovered nucleic acid was mixed with the RT-LAMP amplification reagents from Eiken Co., Ltd. (5 µL of 2×Buffer, 1.09 µL of primers, 0.24 µL of EvaGreen dye, 1.2 µL of Enzyme Mix, and 0.47 µL of water) and amplified at 65° C. for 60 min. The amplification results show that target sequences can be amplified from all four nucleic acid samples extracted from *Staphylococcus aureus* (FIG. 7, (A)-(D)).

Primers for amplification are shown in Table 3.

TABLE 3

| Primer | Sequence | SEQ ID NO: |
|---|---|---|
| Sau-F3 | GTGCCTTTACAGATAGCAT | 39 |
| Sau-B3 | GAAAAAGTGTACGAGTTCTTG | 40 |
| Sau-FIP | GTTTCATAACCTTCAGCAAGCTTTCCATACAGTCATTTCACGC | 41 |
| Sau-BIP | GAGGTCATTGCAGCTTGCTTACTTCGATCACTGGACCGCG | 42 |
| Sau-LF | AACTCATAGTGGCCAACA | 43 |
| Sau-LB | GTACCTGTTATGAAAGTGTTC | 44 |

Example 8

Nucleic Acid Extraction from Galanz Negative Bacteria

The reagents used are as follows.

Lysis buffer: the concentration of guanidine thiocyanate is 6 M, the concentration of TRITON™ X-100 is 5% (v/v), and the pH of the solution is 6.0.

Binding buffer: the concentration of glycogen is 1% (m/v), the concentration of MOPS is 20 mM, the concentration of spermine is 1.5% (m/v), the concentration of TECP is 10 mM, and pH is 9.7.

Wash buffer: the concentration of guanidine hydrochloride is 0.6 M, the concentration of potassium acetate is 0.5 M, the concentration of glycogen is 0.1% (m/v), the concentration of MOPS is 2 mM; the concentration of spermine is 0.3% (m/v), and pH is 5.0.

Enhancer: the concentration of proteinase K is 20 mg/ml, the concentration of trehalose is 6% (m/v), and the concentration of calcium chloride is 5 mM.

Elution buffer: 1×TE buffer with pH of 10.0.

Figure 8:
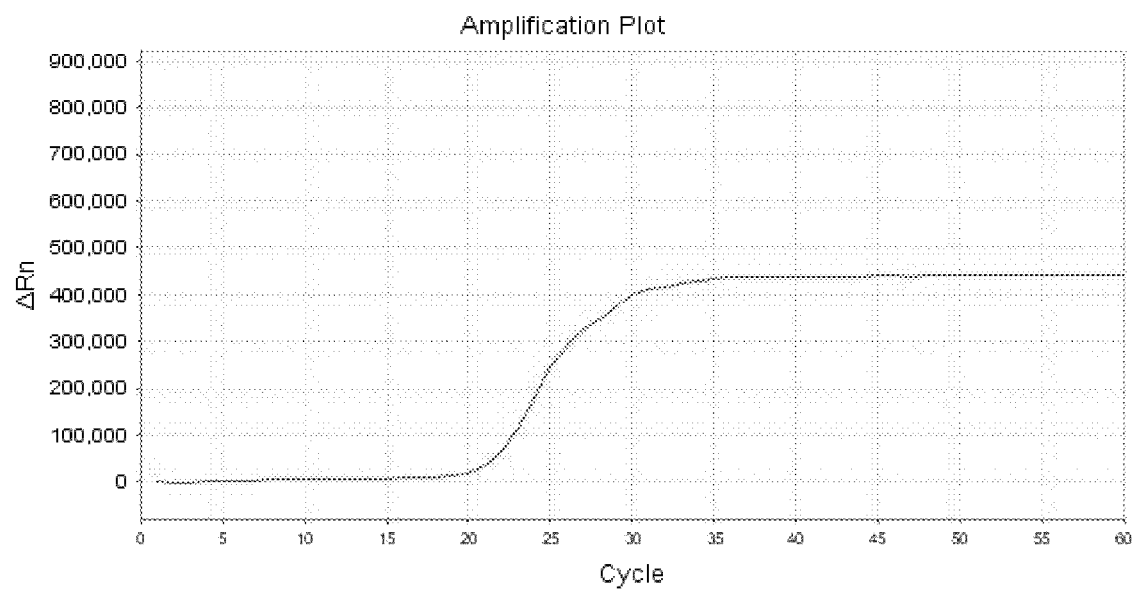
FIG. 8 shows the amplification results of Example 8, in which (A) shows the result from 1E4 copies/μL sample; (B) shows the result from 1E3 copies/μL sample; (C) shows the result from 1E2 copies/μL sample; and (D) shows the result from 1E1 copies/μL sample.
Figure 8:
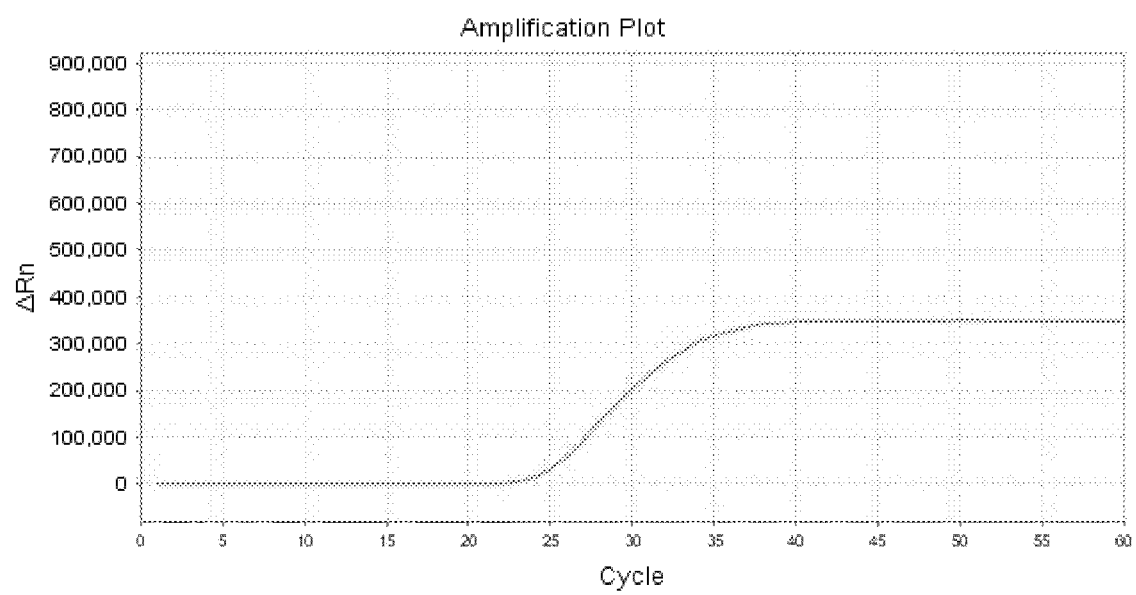
Figure 8:
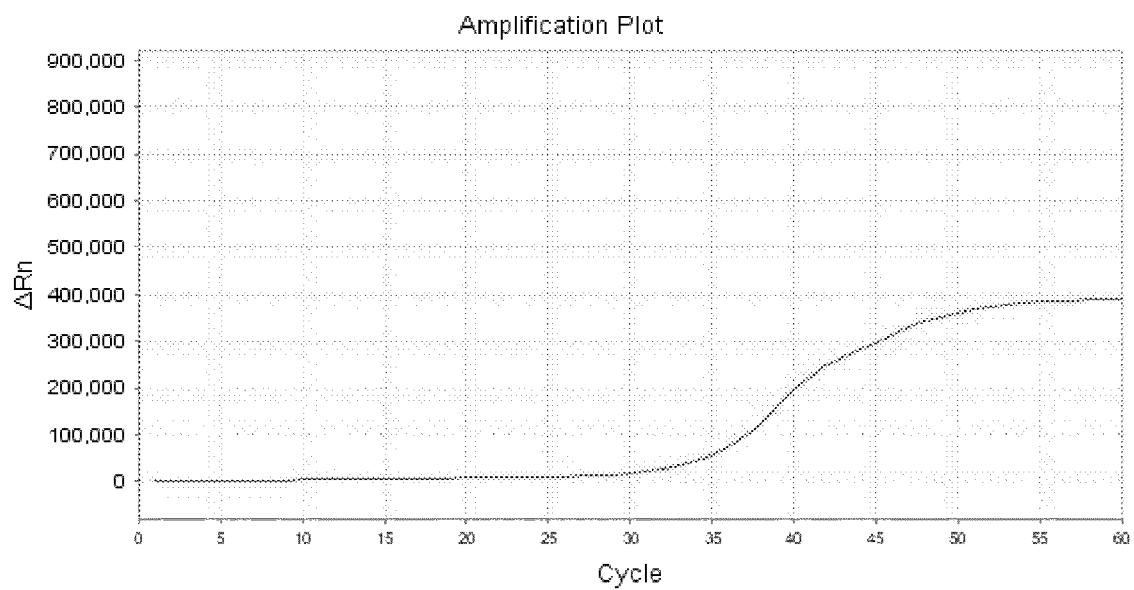
Figure 8:
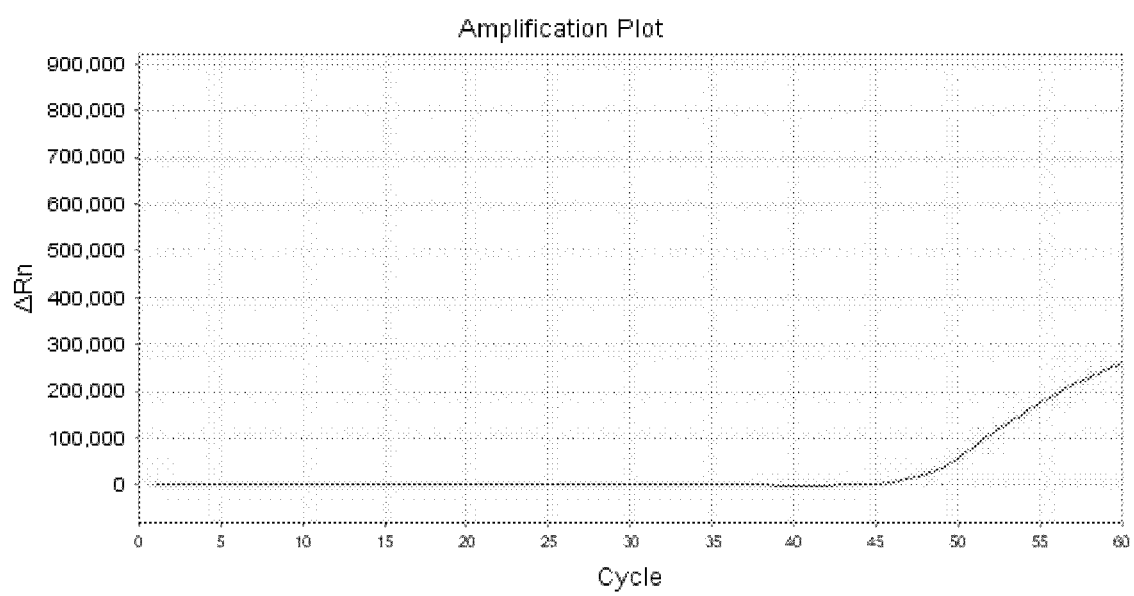

In order to verify the nucleic acid extraction and purification effect of the extraction reagents on Galanz negative bacteria samples, *Escherichia coli* cells were used as the sample to be extracted. 200 μL of cell samples, containing 1E4 copy/μL, 1E3 copy/μL, 1E2 copy/μL and 1E1 copy/μL, were prepared respectively. 200 μL of lysis buffer, 400 μL of binding buffer, and 20 μL of enhancer were added to each tube, mixed and heated at 55° C. for 15 minutes. All the lysed liquid was transferred to an adsorption column, and centrifugation was performed at 13,000 rpm for 40 s. The adsorption column was transferred to a new waste liquid collection tube, into which 200 μL of wash buffer was added, and centrifugation was performed at 13,000 rpm for 40 s. Washing was performed twice, then the waste liquid collection tube was replaced by a nucleic acid collection tube. 50 μL of elution buffer was added to the adsorption column, and centrifugation was performed at 13,000 rpm for 40 s. The adsorption column was discarded, and nucleic acid was recovered. 2 μL of the recovered nucleic acid was mixed with the RT-LAMP amplification reagents from Eiken Co., Ltd. (5 μL of 2×Buffer, 1.09 μL of primers, 0.24 μL of EvaGreen dye, 1.2 μL of Enzyme Mix, and 0.47 μL of water) and amplified at 65° C. for 60 min. The amplification results show that target sequences can be amplified from all four nucleic acid samples extracted from *Escherichia coli* (FIG. 8, (A)-(D)).

Primers for amplification are shown in Table 4.

TABLE 4

| Primer | Sequence | SEQ ID NO: |
|---|---|---|
| Eco-F3 | GCATCGTGGTGATTGATGA | 45 |
| Eco-B3 | GGTTCGTTGGCAATACTC | 46 |
| Eco-FIP | CTTTCGGCTTGTTGCCCGCCTGCTGTCGGCTTTAACCT | 47 |
| Eco-BIP | AGCGAAGAGGCAGTCAACGTTTTGGTTTTTGTCACGCGCTATC | 48 |
| Eco-LF | TCGAAACCAATGCCTAAAG | 49 |
| Eco-LB | GCGCACTTACAGGCGAT | 50 |

Example 9

Nucleic Acid Extraction from Fungus

The reagents used are as follows.

Lysis buffer: the concentration of guanidine thiocyanate is 6 M, the concentration of TRITON™ X-100 is 5% (v/v), and the pH of the solution is 6.0.

Binding buffer: the concentration of glycogen is 1% (m/v), the concentration of MOPS is 20 mM, the concentration of spermine is 1.5% (m/v), the concentration of TECP is 10 mM, and pH is 9.7.

Wash buffer: the concentration of guanidine hydrochloride is 0.6 M, the concentration of potassium acetate is 0.5 M, the concentration of glycogen is 0.1% (m/v), the concentration of MOPS is 2 mM; the concentration of spermine is 0.3% (m/v), and pH is 5.0.

Enhancer: the concentration of proteinase K is 20 mg/ml, the concentration of trehalose is 6% (m/v), and the concentration of calcium chloride is 5 mM.

Elution buffer: 1×TE buffer with pH of 10.0.

Figure 9:
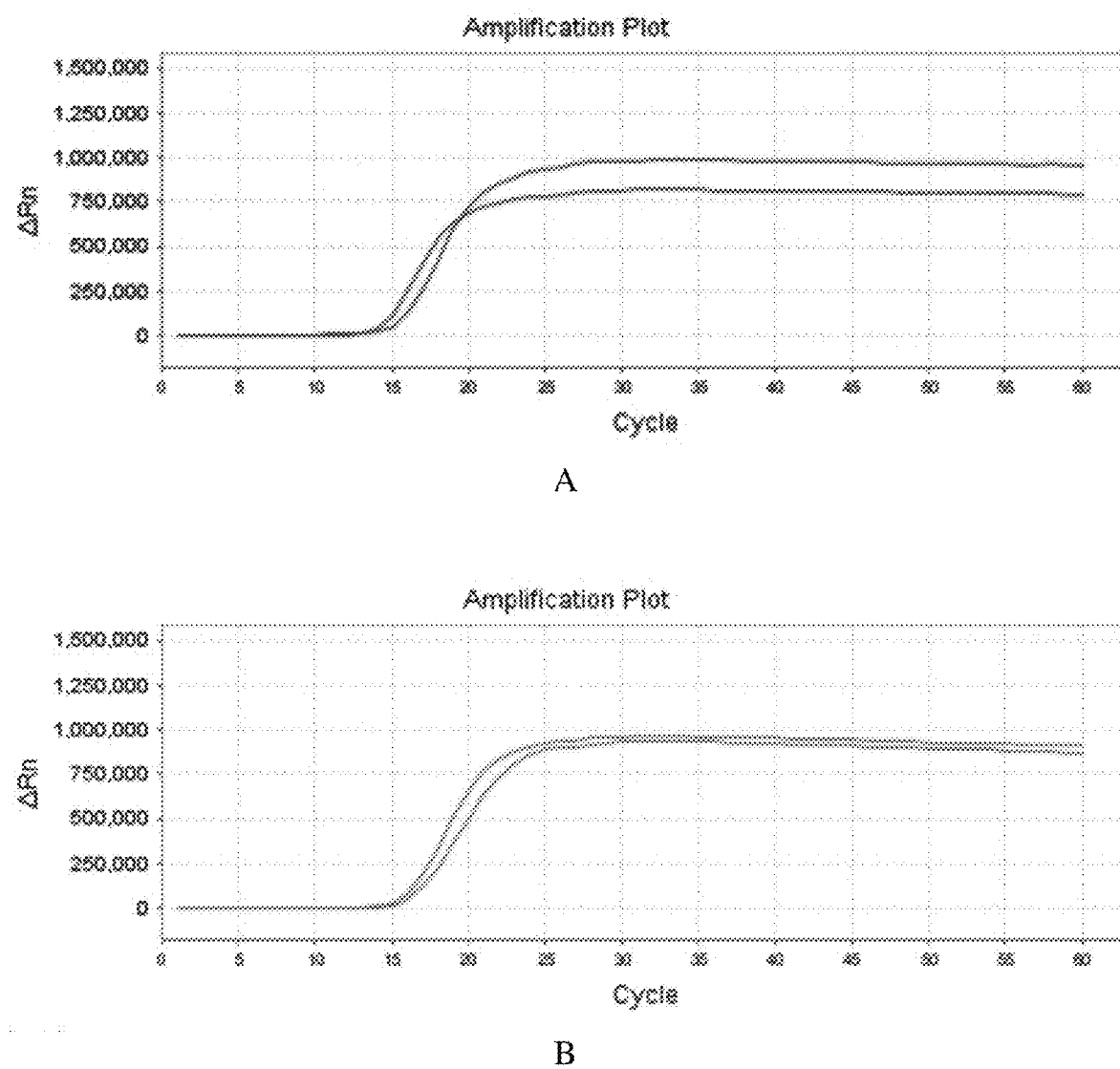
FIG. 9 shows the amplification results of Example 9, in which (A) shows the result from 1E4 copies/μL sample; (B) shows the result from 1E3 copies/μL sample; (C) shows the result from 1E2 copies/μL sample; and (D) shows the result from 1E1 copies/μL sample.
Figure 9:
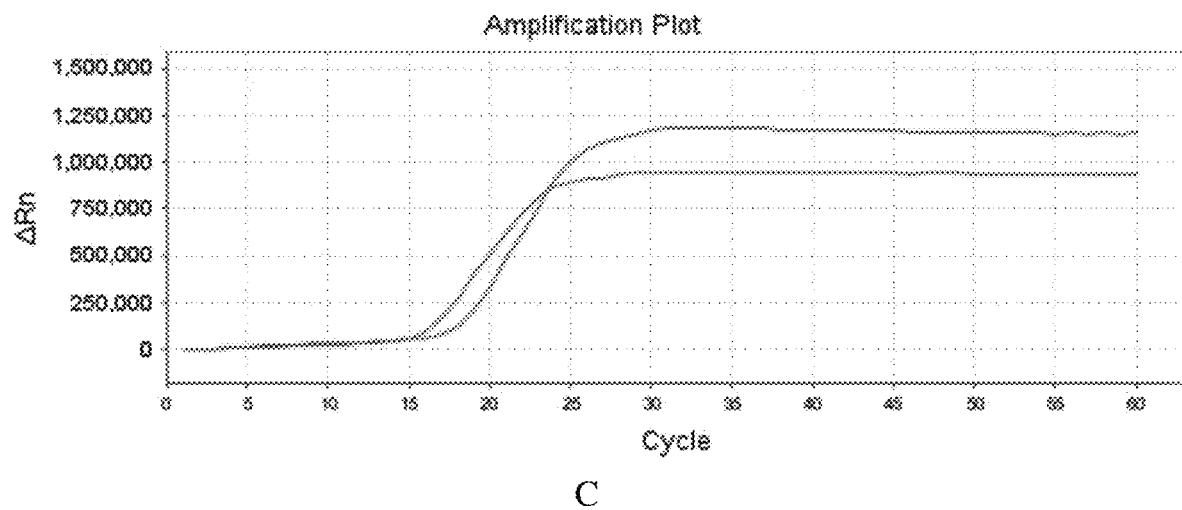
Figure 9:
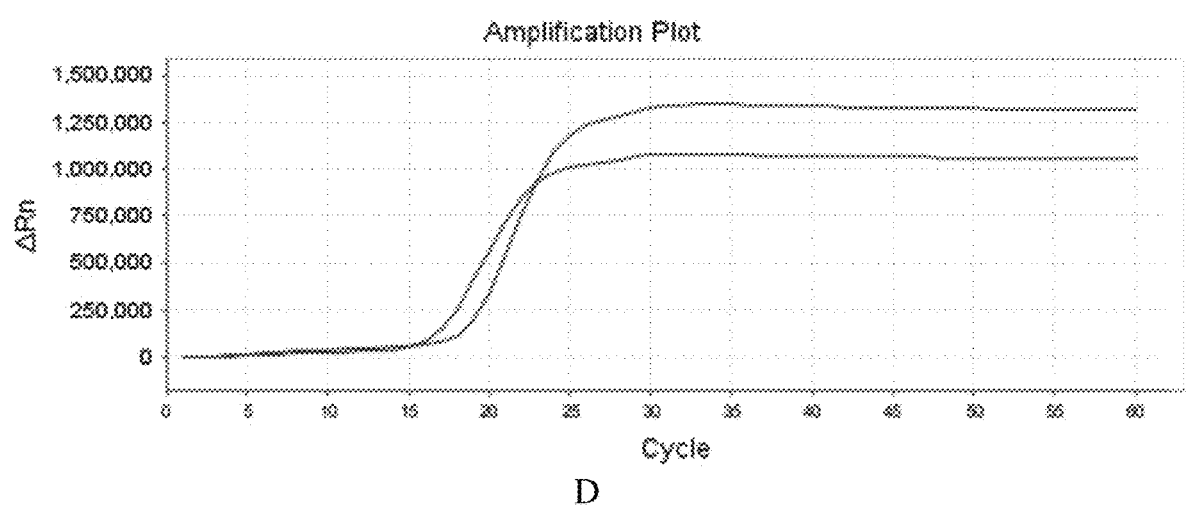

In order to verify the nucleic acid extraction and purification effect of the extraction reagents on fungus samples, yeast cells were used as the sample to be extracted. 200 µL of cell samples, containing 1E4 copy/µL, 1E3 copy/µL, 1E2 copy/µL and 1E1 copy/µL, were prepared respectively. 200 µL of lysis buffer, 400 µL of binding buffer, and 20 µL of enhancer were added to each tube, mixed and heated at 55° C. for 15 minutes. All the lysed liquid was transferred to an adsorption column, and centrifugation was performed at 13,000 rpm for 40 s. The adsorption column was transferred to a new waste liquid collection tube, into which 200 µL of wash buffer was added, and centrifugation was performed at 13,000 rpm for 40 s. Washing was performed twice, then the waste liquid collection tube was replaced by a nucleic acid collection tube. 50 µL of elution buffer was added to the adsorption column, and centrifugation was performed at 13,000 rpm for 40 s. The adsorption column was discarded, and nucleic acid was recovered. 2 µL of the recovered nucleic acid was mixed with the RT-LAMP amplification reagents from Eiken Co., Ltd. (5 µL of 2×Buffer, 1.09 µL of primers, 0.24 µL of EvaGreen dye, 1.2 µL of Enzyme Mix, and 0.47 µL of water) and amplified at 65° C. for 60 min. The amplification results show that target sequences can be amplified from all four nucleic acid samples extracted from yeast (FIG. 9, (A)-(D)).

Primers for amplification are shown in Table 5.

TABLE 5

| Primer | Sequence | SEQ ID NO: |
|---|---|---|
| Yeast-F3 | CCCATCTCACACTCATG | 51 |
| Yeast-B3 | TGGCCAAAACTGCAGCT | 57 |
| Yeast-FIP | CAAGAACAACCCGTCCCCCCTTCCACATTCCACTTAGCG | 53 |
| Yeast-BIP | TAGGAAGCCGTTTTTTTATGCCCCCTGTAGAGAACATTCTTGTG | 54 |
| Yeast-LF | ATAGTAATAATGACTTAA | 55 |
| Yeast-LB | CATCCTTTCATATGTTCC | 56 |

Example 10

Extracted Nucleic Acid Suitable for Amplification Such as LAMP, RT-LAMP, NASBA, PCR and RT-PCR

The reagents used are as follows.

Lysis buffer: the concentration of guanidine thiocyanate is 4 M, the concentration of TRITON™ X-100 is 20% (v/v), and the pH of the solution is 6.0.

Binding buffer: the concentration of glycogen is 0.5% (m/v), the concentration of MOPS is 10 mM, the concentration of spermine is 0.1% (m/v), the concentration of TECP is 6 mM, and pH is 9.5.

Wash buffer: the concentration of guanidine hydrochloride is 0.05 M, the concentration of potassium acetate is 0.15 M, the concentration of glycogen is 0.01% (m/v), the concentration of MOPS is 1 mM, the concentration of spermine is 0.01% (m/v), and pH is 6.0.

Elution buffer: 1×TE buffer with pH of 10.

Enhancer: the concentration of proteinase K is 20 mg/ml, the concentration of trehalose is 6% (m/v), the concentration of calcium chloride is 5 mM.

Figure 10:
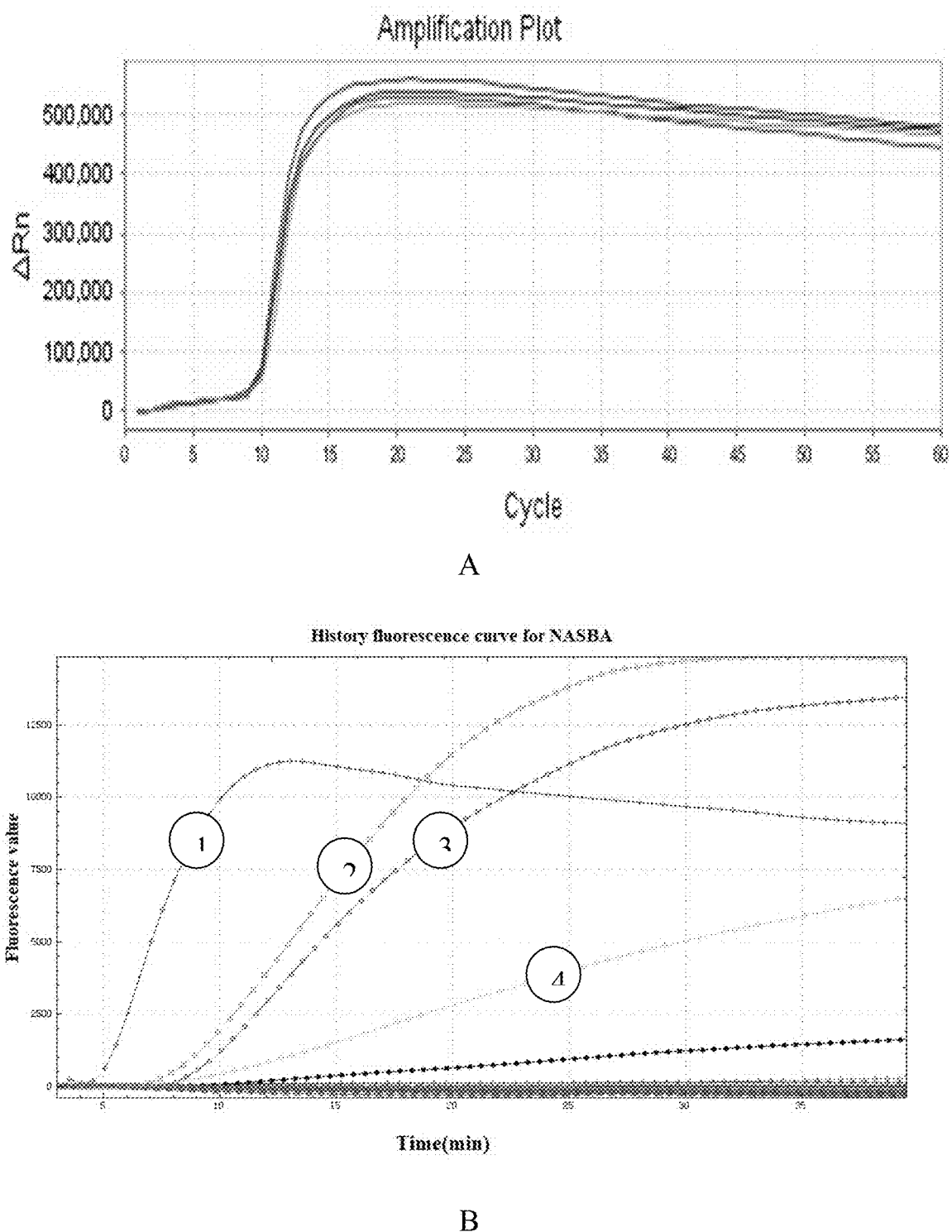
FIG. 10 shows the amplification results of Example 10, in which (A) shows the result of the RT-LAMP amplification (from a saliva sample); (B) shows the result of the NASBA amplification (from a throat swab sample), 1 stands for PC, 2 for influenza A, 3 for influenza A H1N1, and 4 for IC; (C) shows the result of the RT-PCR amplification (from a throat swab sample).
Figure 10:
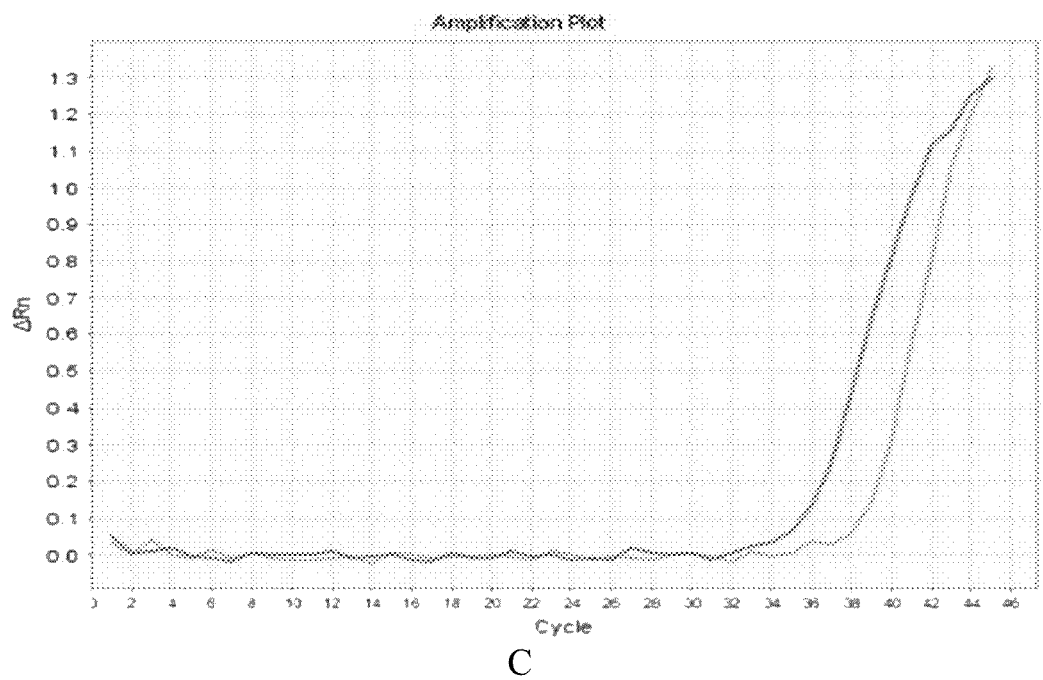

In order to verify whether the nucleic acids extracted by the extraction reagents of the present disclosure may be used in a variety of biological amplification detection, three amplification methods of RT-LAMP, NASBA, and RT-PCR were selected for verification. The extracted nucleic acid used for RT-LAMP was from an influenza-positive sample provided by the International Travel Health Care Center at Beijing Entry and Exit Port. The extracted nucleic acid used for NASBA was from a throat swab preserving fluid sample provided by a hospital, which was extracted by the extraction reagents. The nucleic acid used for RT-PCR was from a throat swab preserving fluid sample provided by a hospital, which was extracted by the extraction reagents. The RT-LAMP amplification system was a commercial kit available from Eiken Co., Ltd., and the RT-LAMP amplification primers were primers for influenza virus developed by CapitalBio Corporation. The amplification system was 5 µL of 2×Buffer, 1.09 µL of primers, 0.24 µL of EvaGreen Dye, 1.2 µL of Enzyme Mix, 0.47 µL of water, 2 µL of the extracted and purified nucleic acid. The detection was performed at 65° C. for 60 min. A virus detection chip produced by CapitalBio Corporation was used in the NASBA amplification, and the ratio of amplification reagent to nucleic acid is 30 µL of the NASBA system to 20 µL of the extracted nucleic acid. Amplification was performed at 42° C. for 45 min. The RT-PCR reagents were the influenza A detection reagents provided by CapitalBio Corporation. In a 20 µL PCR system, 5 µL the extracted and purified template was added. Amplification program was: 48° C. for 20 min, 95° C. for 5 min, then 45 cycles of 95° C. for 10 s and 60° C. for 30 s. The results show that the nucleic acids extracted by the extraction reagents of the present disclosure are suitable for a variety of biological amplification detection methods. The results are shown in FIG. 10, (A)-(C).

```
RT-LAMP primers for influenza virus:
NA1.F3:
TATATACAGTAAAGACAA (as shown in SEQ ID NO: 25);

NA1.B3:
AGAGGGAACTTCACCAATA (as shown in SEQ ID NO: 26);

NA1.FIP:
ATTCCAAGGGGGAGCATGATATCAGTGTAAGAATCGGTTCCAAG (as
shown in SEQ ID NO: 27);

NA1.BIP:
TGCTAAATGACAAACATTCCAATGACAGCTCATTAGGGTTCGAT (as
shown in SEQ ID NO: 28);

NA1.LF:
TGGTTCCCTTATGACAA (as shown in SEQ ID NO: 29);

NA1.LB:
AACCATTAAAGACAGGAGC (as shown in SEQ ID NO: 30).

Sequences of RT-PCR primers:
F:
ACGTACGTTCTCTCTATC (as shown in SEQ ID NO: 31);
and R:
ACTGATTCCCCTAAAATC (as shown in SEQ ID NO: 32).
```

Example 11

Comparison Experiments with Commercial Kit

The reagents used are as follows.

Lysis buffer: the concentration of guanidine thiocyanate is 4 M, the concentration of TRITON™ X-100 is 20% (v/v), and the pH of the solution is 6.0.

Binding buffer: the concentration of glycogen is 0.5% (m/v), the concentration of MOPS is 20 mM, the concentration of spermine is 0.5% (m/v), the concentration of TECP is 6 mM, and pH is 9.5.

Wash buffer: the concentration of guanidine hydrochloride is 0.05 M, the concentration of potassium acetate is 0.15 M, the concentration of glycogen is 0.01% (m/v), the concentration of MOPS is 1 mM, the concentration of spermine is 0.01% (m/v), and pH is 6.0.

Elution buffer: 1×TE buffer with pH of 10.

Enhancer: the concentration of proteinase K is 20 mg/ml; the concentration of trehalose is 6% (m/v), and the concentration of calcium chloride is 5 mM.

In order to compare the different extraction effects between the extraction reagents of the present disclosure and the commercial kit, the QIAamp virus RNA extraction kit (Cat. No. 52904) from QIAGEN was selected for comparison. Both kits were used to extract nucleic acid from 200 µL solutions with 40,000 copies of armored RNA, 4000 copies of armored RNA, 400 copies of armored RNA, and 40 copies of armored RNA, respectively. The elution buffer was 50 µL. Equal amounts of the extracted nucleic acids by these two kits were taken as a template, and amplified using the RT-LAMP amplification system prepared in the same batch.

Figure 11:
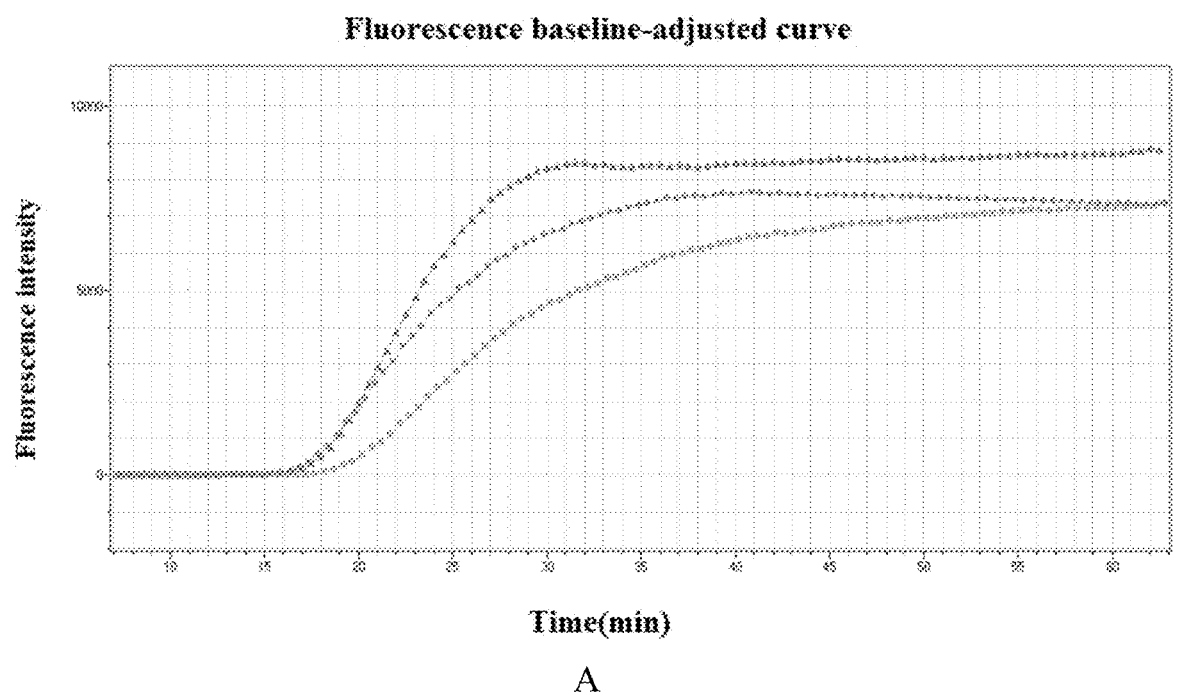
FIG. 11 shows the amplification results of Example 11, in which (A) shows the result from 4000 copies sample by QIAGEN; (B) shows the result from 4000 copies sample by this method; (C) shows the result from 400 copies sample by QIAGEN; (D) shows the result from 400 copies sample by this method; (E) shows the result from 40 copies sample by QIAGEN; and (F) shows the result from 40 copies sample by this method.
Figure 11:
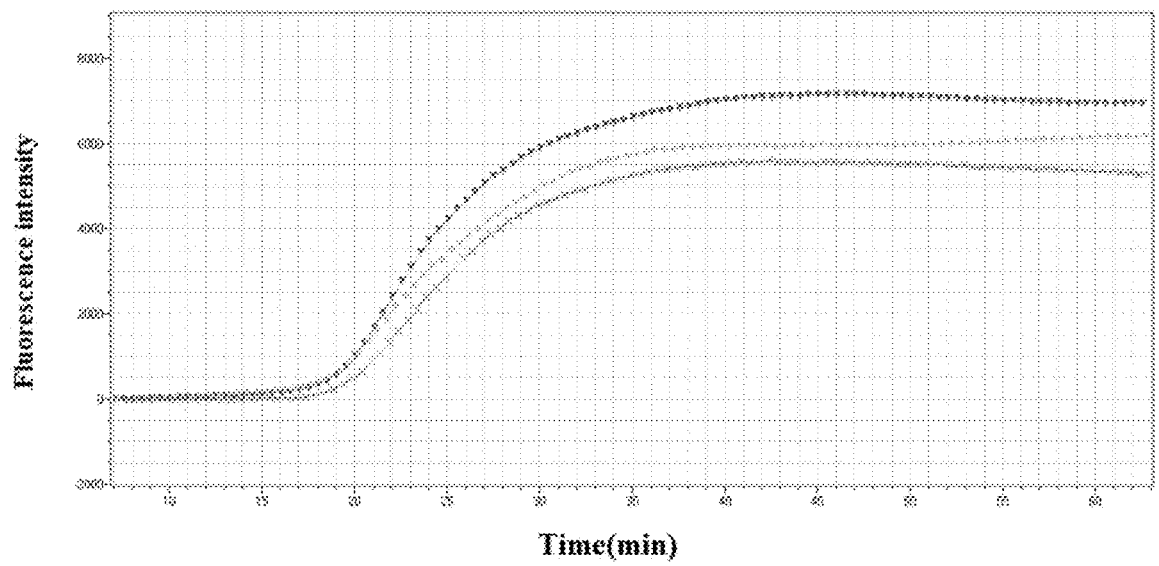
Figure 11:
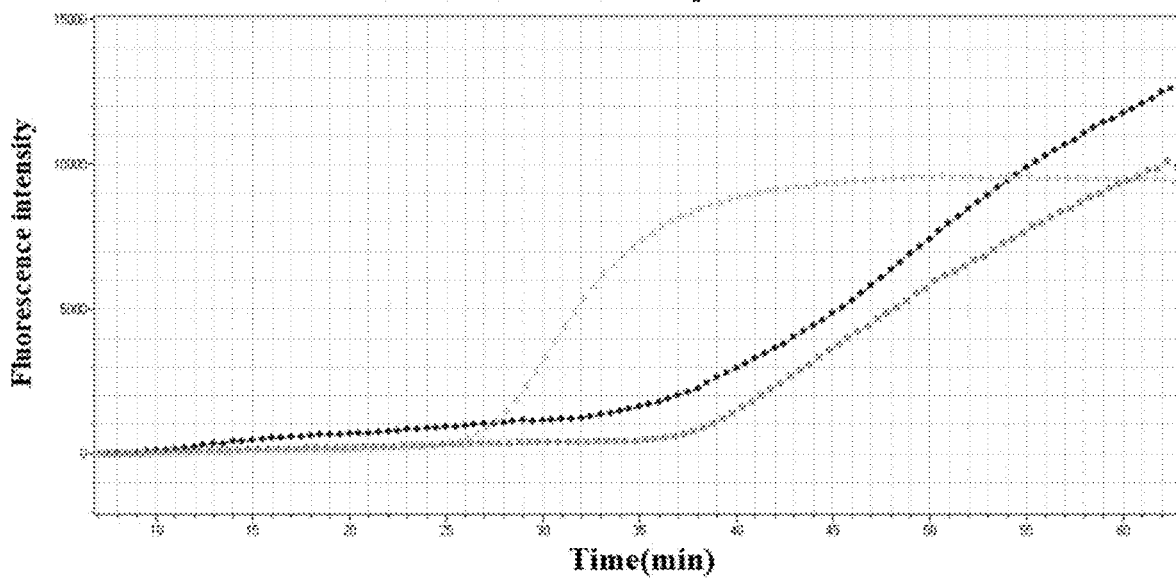
Figure 11:
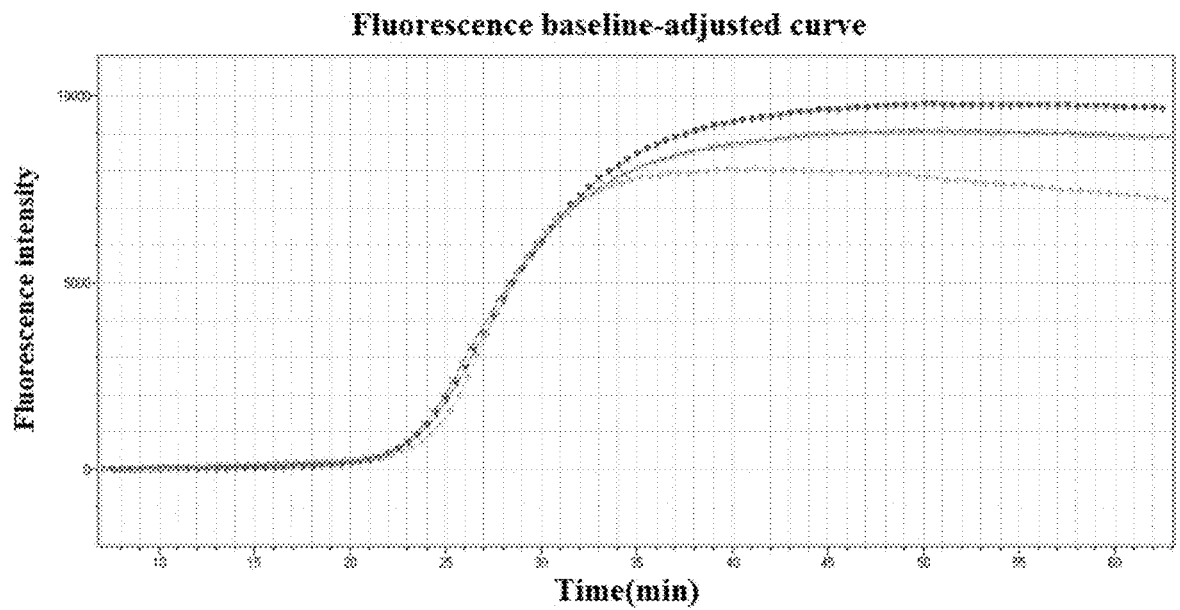
Figure 11:
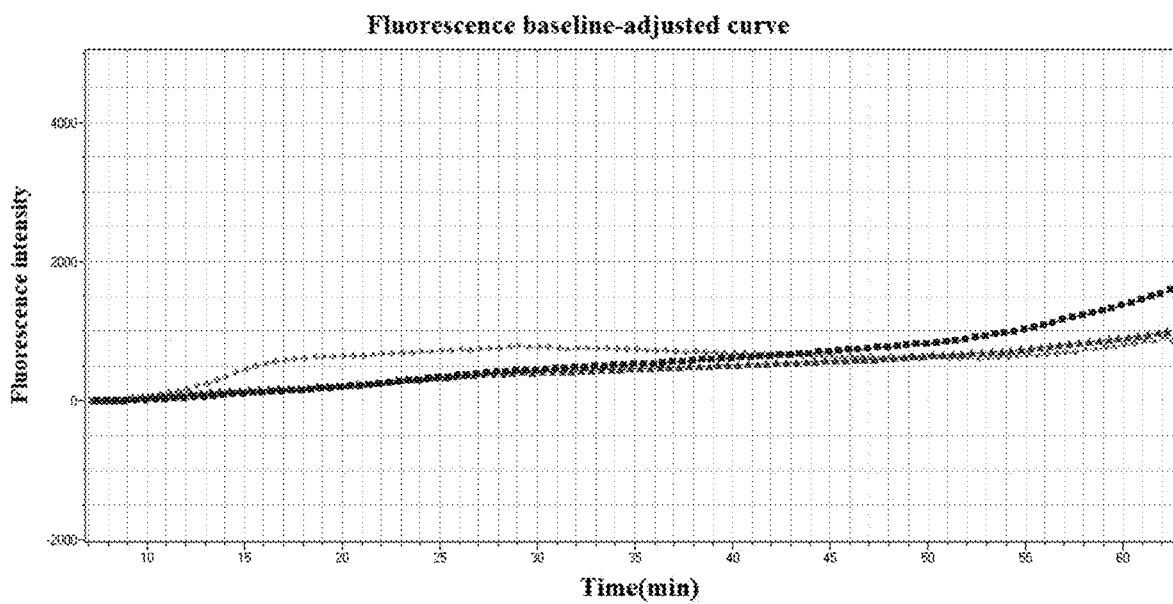
Figure 11:
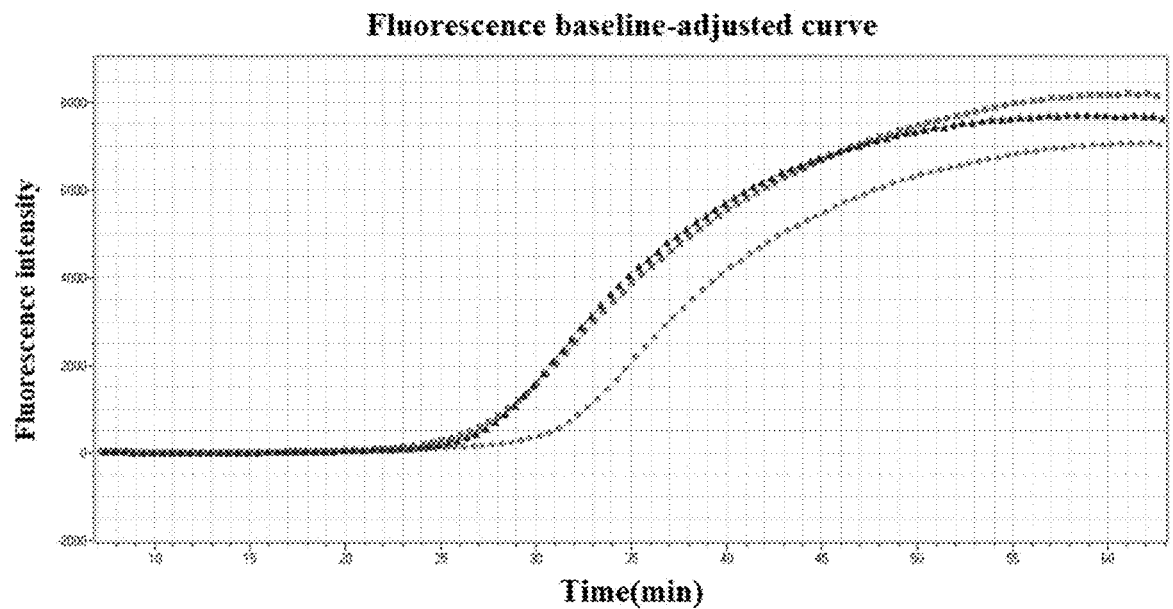

The extraction protocol of the QIAGEN kit was as follows. 25 µL of PK, 200 µL of armored RNA and 200 µL of Buffer AL were mixed at 56° C. for 15 min. After a short spin, 250 µL of absolute ethanol was added, shaked and mixed, leaving it stand at room temperature for 5 min. After a short spin, the obtained liquid was added to a adsorption column. After centrifugation for 1 min, the waste liquid and waste tube were discarded, then 500 µL of AW1 was added. After centrifugation for 1 min, the waste liquid and waste tube were discarded, then 500 µL of AW2 was added. After centrifugation for 1 min, the waste liquid and waste tube were discarded, then 500 µL of absolute ethanol was added. After centrifugation for 1 min, the waste liquid and waste tube were discarded. After centrifugation for 3 min (13,000 rpm), the waste liquid and waste tube were discarded, and the tube was opened at 56° C. for 3 min to dry the silicon membrane. Another 1.5 ml centrifuge tube was used for collection, into which 50 µL of Buffer ATE was added and incubated at room temperature for 1 min. Centrifugation was performed for 1 min (13,000 rpm). The resultant was stored at −20° C. The amplification results show that the nucleic acid extracted by the extraction reagents of the present disclosure is equivalent to QIAGEN's kit when using for high concentration of virus (4000 copies), and is better than QIAGEN when using for low concentration of virus (400 copies, 40 copies). The experimental results are shown in FIG. 11, (A)-(F).

Example 12

Specificity Test

The nucleic acid extraction reagents comprise the followings.

Lysis buffer: the concentration of guanidine isothiocyanate is 4 M, the concentration of TRITON™ X-100 is 20% (v/v), and the pH of the solution is 6.0.

Binding buffer: the concentration of glycogen is 0.3% (m/v), the concentration of MOPS is 20 mM, the concentration of spermine is 0.5% (m/v), the concentration of TECP is 6 mM, and pH is 9.5.

Wash buffer: the concentration of guanidine hydrochloride of 0.15 M, the concentration of potassium acetate of 0.15 M, the concentration of glycogen of 0.05% (m/v), the concentration of MOPS is 2 mM, the concentration of spermine of 0.1% (m/v), and pH is 6.0.

Enhancer: the concentration of proteinase K is 20 mg/ml, the concentration of trehalose is 6% (m/v), and the concentration of calcium chloride is 5 mM.

In order to investigate the specificity of nucleic acid extraction reagents of the present disclosure, 200 μL of saliva (from a healthy employee of CapitalBio Corporation), 200 μL of lysis buffer, 400 μL of binding buffer, and 20 μL of enhancer were mixed and transferred to a column. The column was washed twice with 200 μL of wash buffer and eluted with 50 μL of elution buffer. The eluate was used as a template and subjected to LAMP for the detection of EV71, duck plague virus, and influenza A H1N1. The amplification system was 5 μL of 2×Buffer, 1.09 μL of primers, 0.24 μL of EvaGreen dye, 1.2 μL of Enzyme Mix, 0.47 μL of water, and 2 μL of the extracted sample. Detection was performed at 65° C. for 40 min.

Figure 12:
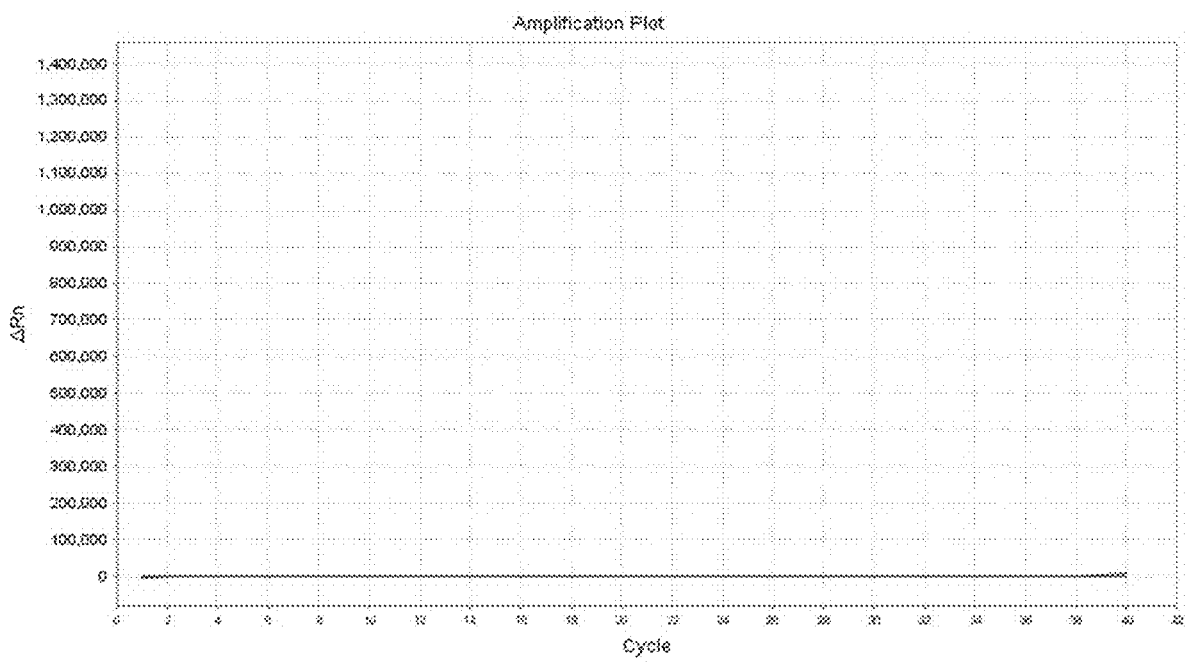
FIG. 12 shows the amplification results of Example 12, in which (A) shows the result of the EV71 amplification; (B) shows the result of the duck plague virus amplification; (C) shows the result of the influenza A H1N1 amplification.
Figure 12:
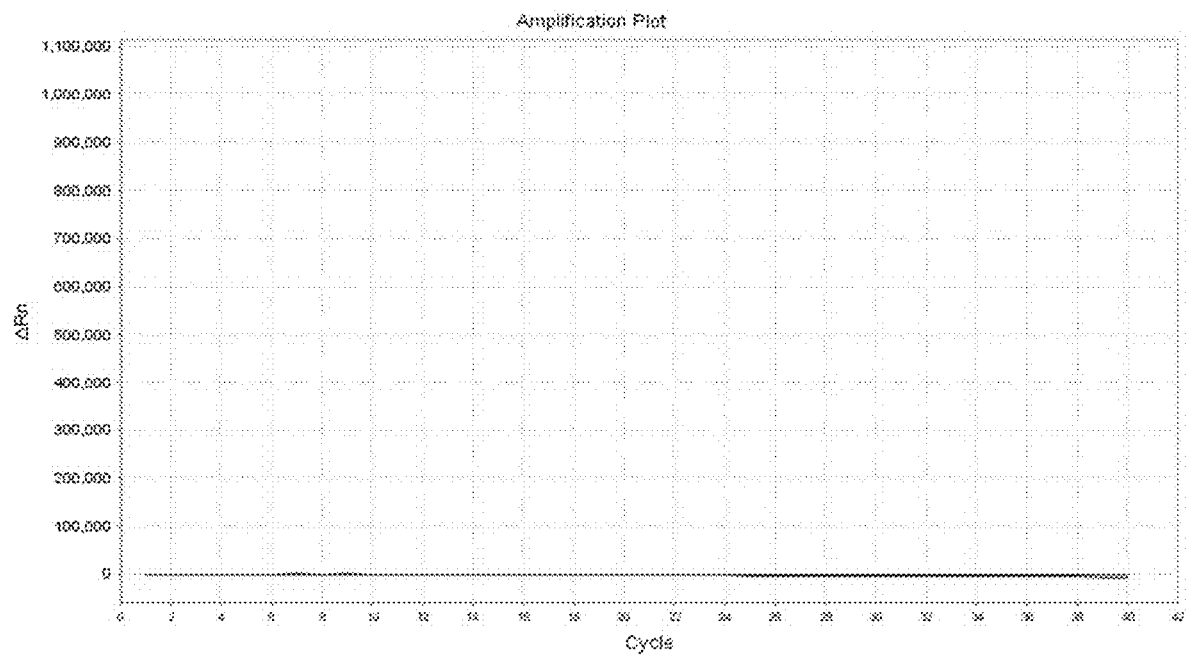
Figure 12:
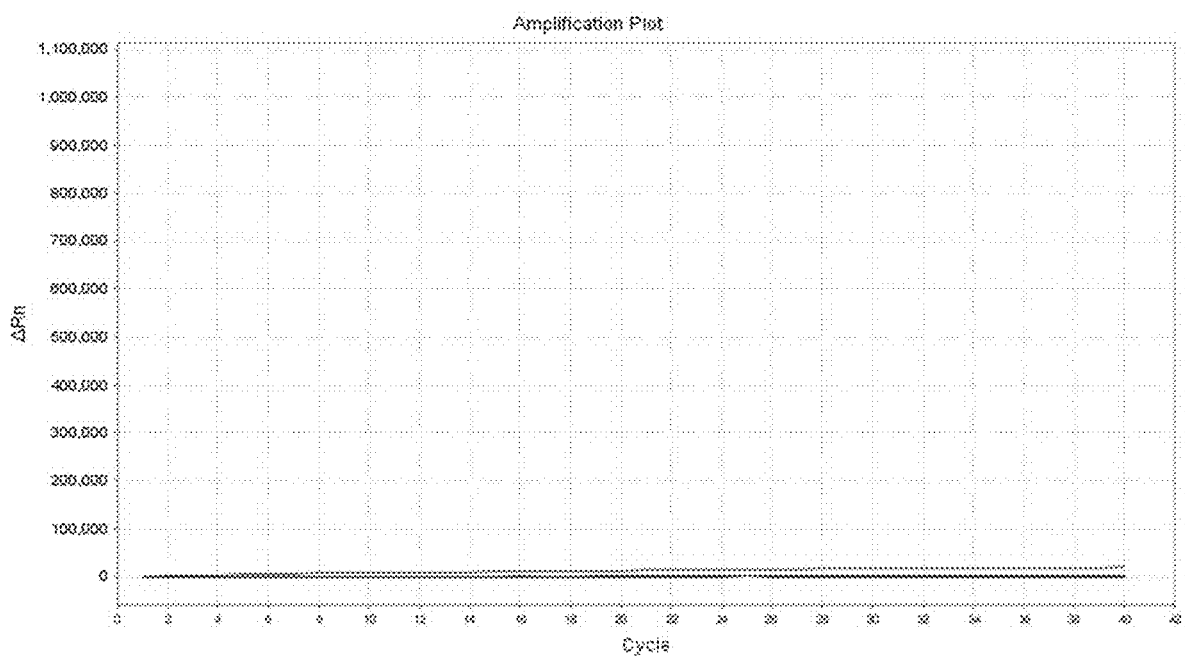

The results show that none of the peaks corresponding to EV71, duck plague virus, and influenza A H1N1 appeared, indicating that the nucleic acid extracted by the nucleic acid extraction and purification reagent has good specificity. The results are shown in FIG. 12, (A)-(C).

Example 13

Use of the Reagents in Enclosed Integrated Chip

Figure 13:
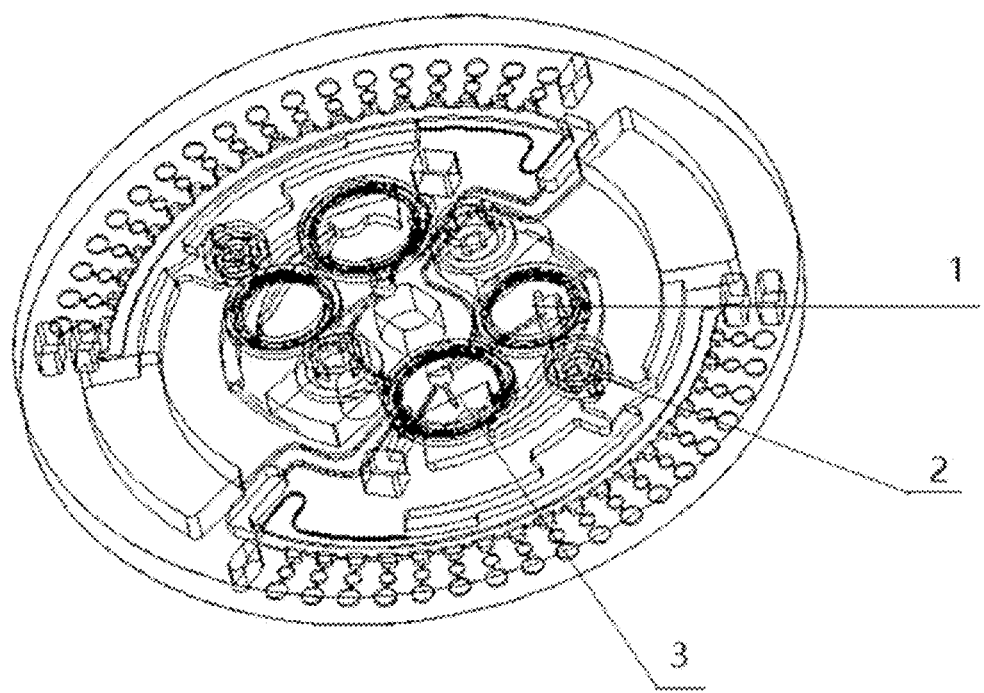
FIG. 13 shows a schematic diagram of the liquid reagent storage on an integrated chip of Example 13, in which 1—the wash buffer storage part, 2—the binding buffer and enhancer storage part, and 3—the elution buffer storage part.
Figure 14:
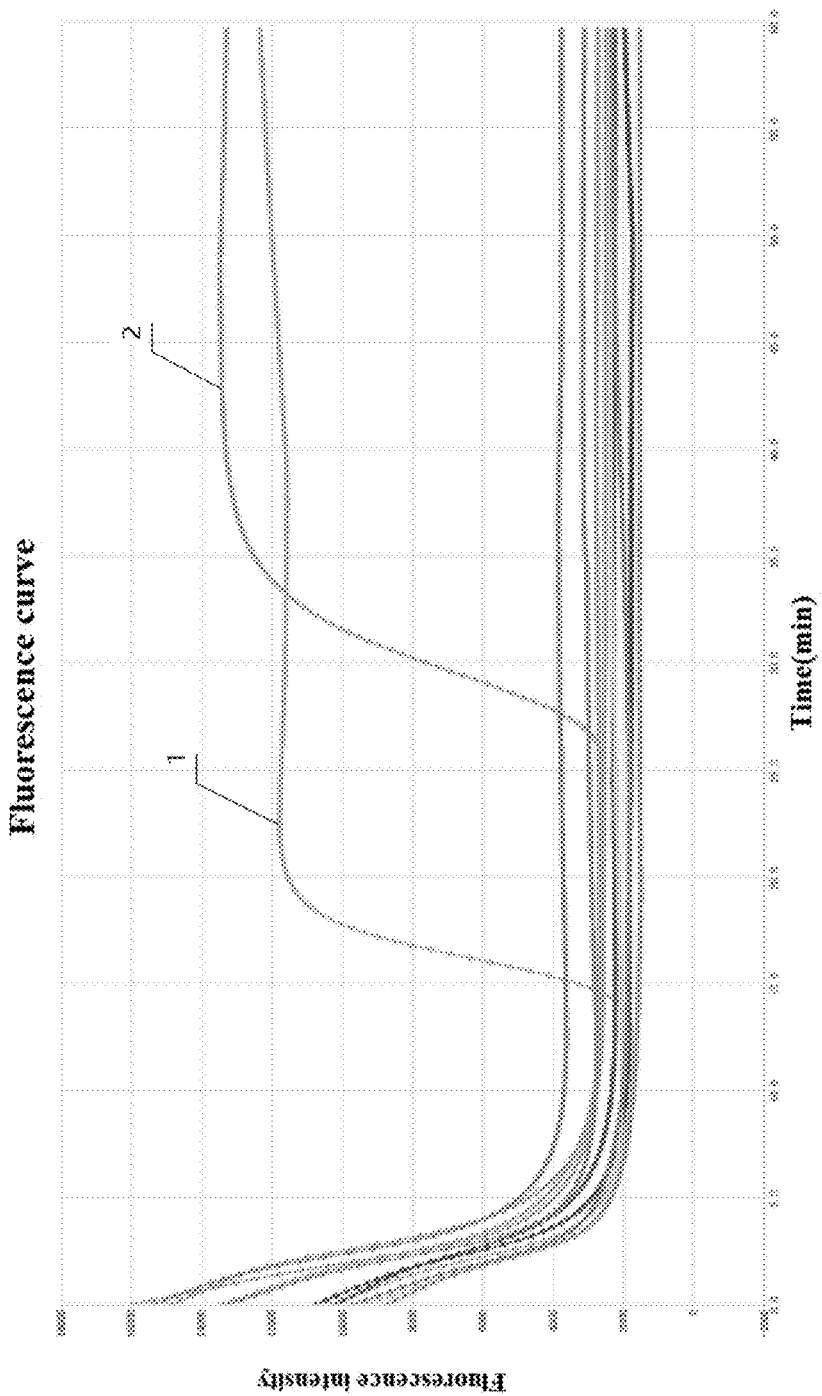
FIG. 14 shows the test results of Example 13, in which amplification curve 1-positive external control (duck plague virus nucleic acid), and 2-influenza A H1N1 gene.

The wash buffer and the elution buffer provided in Example 1 of the present disclosure were stored as a liquid in a fully integrated chip, and the binding buffer and the enhancer were stored in a form of freeze-dried solid on the chip. 600 μL of influenza A positive saliva sample (from Beijing International Travel Health Care Center) was mixed with 200 μL of lysis buffer and all the mixture was added to the fully enclosed integrated chip for detection. The chip was put into an instrument for automatic detection. The schematic diagram of the liquid reagent storage of the integrated chip is shown in FIG. 13 and the test results are shown in FIG. 14.

The above are only the preferred embodiments of the present disclosure. It should be pointed out that for those of ordinary skill in the art, several improvements and modifications can be made without departing from the principle of the present disclosure, and these improvements and modifications should also be regarded as the protection scope of the present disclosure.

What is claimed is:

1. A nucleic acid extraction composition comprising a binding buffer, a wash buffer, a lysis buffer, an enhancer, and an elution buffer, wherein
the binding buffer is a composition comprising glycogen, 3-(Morpholin-4-yl)propane-1-sulfonic acid (MOPS), polyamine, and tris(2-carboxyethyl)phosphine (TCEP); the wash buffer is a composition comprising guanidine hydrochloride, potassium acetate, glycogen, MOPS, and polyamine;
in the binding buffer, the concentration of glycogen is 0.1% to 1% (m/v), the concentration of MOPS is 10 mM to 20 mM, the concentration of polyamine is 0.1% to 2% (m/v), and the concentration of TCEP is 5 mM to 50 mM; the polyamine comprises spermine, spermidine, butanediamine or a mixture thereof; and the pH of the binding buffer is 8.5 to 10;
in the wash buffer, the concentration of guanidine hydrochloride is 0.05 M to 0.6 M, the concentration of potassium acetate is 0.05 M to 0.5 M, the concentration of glycogen is 0.01% to 0.1% (m/v), the concentration of MOPS is 1 mM to 2 mM, and the concentration of polyamine is 0.01% to 0.3% (m/v); the polyamine comprises spermine, spermidine, butanediamine or a mixture thereof; and the pH of the wash buffer is 5 to 6;
the lysis buffer comprises guanidine isothiocyanate, 2-[4-(2,4,4-trimethylpentan-2-yl)phenoxy]ethanol or a mixture thereof; and in the lysis buffer, the concentration of guanidine isothiocyanate is 2 M to 8 M, the concentration of 2-[4-(2,4,4-trimethylpentan-2-yl)phenoxy]ethanol is 5% to 20% (v/v), and the pH value is 3 to 6;
the enhancer comprises proteinase K, trehalose, calcium chloride or a mixture thereof; and in the enhancer, the concentration of proteinase K is 10 mg/ml to 25 mg/ml, the concentration of trehalose is 3% to 12% (m/v), and the concentration of calcium chloride is 5 mM to 20 mM;
the elution buffer comprises sodium hydroxide, 1×Tris-EDTA (TE) buffer or a mixture thereof; the pH of 1×TE buffer in the elution buffer is adjusted to 8 to 10 with sodium hydroxide; and
the nucleic acid extraction composition does not comprise volatile organic solvents.

2. A kit for nucleic acid extraction or nucleic acid detection comprising the nucleic acid extraction composition according to claim 1 and a reagent or carrier acceptable for extraction and/or detection.

3. The kit according to claim 2, wherein the carrier is selected from the group consisting of a silicon-based adsorption column, magnetic beads, glass beads, and a chitosan or silica modified carrier.

4. A method for nucleic acid extraction or detection for non-diagnostic purposes comprising
mixing a nucleic acid sample to be tested with the nucleic acid extraction composition according to claim 1; and performing extraction and/or detection.

\* \* \* \* \*